US010252996B2

(12) United States Patent
Min et al.

(10) Patent No.: US 10,252,996 B2
(45) Date of Patent: *Apr. 9, 2019

(54) N1-CYCLIC AMINE-N5-SUBSTITUTED BIGUANIDE DERIVATIVES, METHODS OF PREPARING THE SAME AND PHARMACEUTICAL COMPOSITION COMPRISING THE SAME

(71) Applicant: Immunomet Therapeutics Inc., Houston, TX (US)

(72) Inventors: Chang Hee Min, Seoul (KR); Yong Eun Kim, Daejeon (KR); Byung Kyu Oh, Chungcheongnam-do (KR); Ji Sun Lee, Daejeon (KR); Hye Jin Heo, Daejeon (KR); Ju Hoon Oh, Gangwon-do (KR); Woong Cho, Daejeon (KR)

(73) Assignee: ImmunoMet Therapeutics Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,971

(22) Filed: Dec. 14, 2017

(65) Prior Publication Data

US 2018/0105494 A1    Apr. 19, 2018

Related U.S. Application Data

(62) Division of application No. 14/766,203, filed as application No. PCT/KR2014/001006 on Feb. 6, 2014, now Pat. No. 9,884,821.

(30) Foreign Application Priority Data

Feb. 7, 2013   (KR) .................. 10-2013-0014175
Feb. 7, 2013   (KR) .................. 10-2013-0014176

(51) Int. Cl.
| C07D 207/20 | (2006.01) |
| C07D 211/14 | (2006.01) |
| C07D 211/16 | (2006.01) |
| C07D 211/70 | (2006.01) |

(52) U.S. Cl.
CPC .......... *C07D 211/70* (2013.01); *C07D 207/20* (2013.01); *C07D 211/14* (2013.01); *C07D 211/16* (2013.01)

(58) Field of Classification Search
CPC ... C07D 211/14; C07D 211/70; C07D 211/16; C07D 207/20
USPC ....................................................... 546/184
See application file for complete search history.

(56) References Cited

U.S. PATENT DOCUMENTS

| 2,467,371 A | 4/1949 | Swinden et al. |
| 3,960,949 A | 6/1976 | Ahrens et al. |
| 7,622,117 B2 | 11/2009 | Tobia et al. |
| 9,133,110 B2 | 9/2015 | Kim et al. |
| 9,321,742 B2 | 4/2016 | Kim et al. |
| 9,416,098 B2 * | 8/2016 | Kim .................. C07C 279/26 |
| 9,464,042 B2 * | 10/2016 | Kim .................. C07C 279/26 |
| 9,539,238 B2 | 1/2017 | Kang et al. |
| 9,540,325 B2 | 1/2017 | Kim et al. |
| 9,884,821 B2 * | 2/2018 | Min .................. C07D 211/16 |
| 9,993,446 B2 * | 6/2018 | Kim .................. C07C 279/26 |
| 10,058,558 B2 * | 8/2018 | Kim .................. A61K 31/155 |
| 2012/0135952 A1 | 5/2012 | Kim et al. |
| 2012/0283299 A1 | 11/2012 | Kim et al. |
| 2012/0309799 A1 | 12/2012 | Kim et al. |
| 2014/0179660 A1 | 6/2014 | Kim et al. |
| 2014/0179661 A1 | 6/2014 | Kim et al. |
| 2014/0235558 A1 | 8/2014 | Kim et al. |
| 2014/0235559 A1 | 8/2014 | Kim et al. |
| 2015/0126518 A1 | 5/2015 | Kim et al. |
| 2015/0376123 A1 | 12/2015 | Kim et al. |
| 2016/0101112 A1 | 4/2016 | Kim et al. |
| 2016/0317478 A1 | 11/2016 | Kim et al. |
| 2016/0331724 A1 | 11/2016 | Kang et al. |
| 2017/0073331 A1 | 3/2017 | Kim et al. |
| 2018/0044283 A1 * | 2/2018 | Kim .................. C07C 279/26 |
| 2018/0093953 A1 * | 4/2018 | Kim .................. C07D 211/38 |

FOREIGN PATENT DOCUMENTS

| GB | 599714 A | 3/1948 |
| KR | 10-2013-0018622 | 2/2013 |
| KR | 10-2013-0019351 | 2/2013 |
| KR | 10-2011-0081093 | 6/2013 |
| WO | WO-92/07560 A1 | 5/1992 |
| WO | WO-2005/079463 A2 | 9/2005 |

(Continued)

OTHER PUBLICATIONS

Boggiano et al., "Hypoglycaemic agents. Part I," Journal of Pharmacy and Pharmacology, 13:567-574 (1961).

Boutet et al., "Snail activation disrupts tissue homeostasis and induces fibrosis in the adult kidney," EMBO J. 25(23):5603-13 (2006).

Brzozowski et al., "Synthesis and diuretic properties of certain derivatives of 1-phenyl-3-(3,5,5-trimethyl-2-pyrazoline-1-carboimidoyl)guanidine," Acta Poloniae Pharmaceutica 36:645-650 (1979) (English language translation provided).

Chemical Abstracts STN Registry Database record for RN 1092281-51-0 entered Dec. 31, 2008.

Chemical Abstracts STN Registry Database records for RN 1349886-10-7 and RN 1347987-36-3, entered Dec. 6, 2011 and Dec. 4, 2011.

Curd et al., "Synthetic antimalarials. Part X. Some aryl-diguanide ("-biguanide") derivatives," Journal of the Chemical Society pp. 729-737 (1946).

(Continued)

*Primary Examiner* — Daniel R Carcanague

(74) *Attorney, Agent, or Firm* — Clark & Elbing LLP

(57) ABSTRACT

The present invention provides an N1-cyclic amine-N5-substituted biguanide derivative compound represented by Formula 1, a method of preparing the same and a pharmaceutical composition including the biguanide derivative or the pharmaceutically acceptable salt thereof as an active ingredient. The biguanide derivatives have an effect of inhibiting cancer cell proliferation, cancer metastasis and cancer recurrence by activation of AMPK, even when administered in a small dose compared with conventional drugs.

5 Claims, No Drawings

(56) References Cited

FOREIGN PATENT DOCUMENTS

| WO | WO-2013/022278 A2 | 2/2013 |
| WO | WO-2013/022279 A2 | 2/2013 |
| WO | WO-2013/188452 A1 | 12/2013 |
| WO | WO 2016/080810 A2 | 5/2016 |

OTHER PUBLICATIONS

Derynck et al., "Differentiation plasticity regulated by TGF-beta family proteins in development and disease," Nat Cell Biol. 9(9):1000-4 (2007).

Dowling et al., "Undertanding the benefit of metformin use in cancer treatment," BMC Medicine 9-33 (2013).

Hutchison et al., "Resident mesenchymal cells and fibrosis," available in PMC Jul. 1, 2014, published in final edited form as: Biochim Biophys Acta. 1832(7):962-71 (2013) (21 pages).

James et al., "The synthesis of some heterocyclic derivatives of biguanide with antibacterial activity," J Med Chem. 11:942-945 (1968).

Rattan et al., "Metoformin: an emerging new therapeutic option for targeting cancer stem cells and metastasis," Journal of Oncology Article ID 928127, 12 pages (2012).

Russo et al., AMP-activated protein kinase: a target for old drugs against diabetes and cancer, Biochem Pharmacol. 86:339-350 (2013).

Shapiro et al., "Hypoglycemic agents. III. N1-alykyl- and aralkylbiguanides," J Am Chem Soc. 1959, 81:3728-3736 (1959).

Tak, "Investigation of the Antifibrotic Effect of Erythropoietin (EPO) from Hepatic Cirrhosis Animal model," Clin Mol Hepatol. 13(4S);S74-8 (2007).

Willis et al., "TGF-beta-induced EMT: mechanisms and implications for fibrotic lung disease," Am J Physiol Lung Cell Mol Physiol. 293(3):L525-34 (2007).

Extended European Search Report for Application No. 14748929.8, dated Sep. 28, 2016, 9 pages.

International Search Report for International Application No. PCT/KR2014/004474, dated Aug. 7, 2014 (6 pages).

* cited by examiner

N1-CYCLIC AMINE-N5-SUBSTITUTED BIGUANIDE DERIVATIVES, METHODS OF PREPARING THE SAME AND PHARMACEUTICAL COMPOSITION COMPRISING THE SAME

TECHNICAL FIELD

The present invention relates to an N1-cyclic amine-N5-substituted biguanide derivative that inhibits cancer cell proliferation, cancer metastasis and cancer recurrence by activation of AMPK, even when administered in a small dose compared with conventional drugs, and that exhibits excellent therapeutic effects, a method of preparing the same, and a pharmaceutical composition including the N1-cyclic amine-N5-substituted biguanide derivative as an active ingredient.

BACKGROUND ART

AMPK (AMP-activated protein kinases) is an enzyme that functions to regulate a metabolic pathway so as to maintain balance between supply of nutrients and demand for energy, and thus maintain energy homeostasis in cells and the whole body. AMPK is activated as a ratio of AMP/ATP in the cells increases due to a hypoxemic state or glucose deficiency. The activated AMPK induces fatty acid oxidation to produce a larger amount of ATP and inhibits anabolisms requiring the use of ATP. AMPK inhibits proliferation of cancer cells and kills the cancer cells by regulating energy metabolism in the cancer cells as well as in normal cells. AMPK activated in the cancer cells shows anticancer activities by phosphorylating mTORC1, p53, fatty acid synthase and the like to regulate the cell cycle, cell polarity, autophagy, apoptosis, etc.

Metformin has been used to treat insulin-independent diabetes mellitus (i.e., type II diabetes mellitus) since, among oral therapeutic agents for treating diabetes mellitus, it is most effective at lowering blood glucose, does not cause hypoglycemia or hyperinsulinemia and can prevent complications. In recent years, metformin has been extensively researched. Also, it was reported that metformin activates AMP-activated protein kinase (AMPK) by inhibiting the action of complex 1 of the electron transport system in mitochondria to obstruct intracellular generation of energy, and inhibits activation of the mTOR/S6K1 signaling pathway in which proteins essential for survival are produced to obstruct proliferation of cancer cells and tumor growth (Mol. Cancer Ther. 9(5): 1092-1099 (2010)). Consequently, metformin has received considerable attention as an anticancer agent for regulating cancer cell metabolism. Also, an epidemiological survey confirmed that the incidence of cancer and mortality by cancer were lower for patients treated with metformin (BMJ. 330: 1304-1305 (2005)).

Meanwhile, there is increasing clinical evidence indicating that cancer stem cells take part in recurrence and metastasis of cancer. The cancer stem cells refer to cancer cells that have self-regeneration or differentiation activities which are characteristically innate to stem cells. The cancer stem cells are present in the cancer tissues at a content of 0.2% or less, and are characterized by their slow proliferation. Since many anticancer agents developed so far target cancer cells that proliferate rapidly, the cancer stem cells are resistant to conventional anticancer therapy when cancer stem cells are treated with the anticancer agents, thereby causing poor prognoses. On the other hand, it was reported that metformin prevents the recurrence of cancer as it selectively acts only on cancer stem cells among breast cancer cells and removes the cancer stem cells (Cancer Res. 69(19): 7507-11 (2009)). Also, it was found that metformin prevents the metastasis of cancer by interfering with the motility and invasion of the cancer since it inhibits the expression of Snail1, Slug, Twist, ZEB ½ and TGF-b, which are transcription factors associated with the epithelial-to-mesenchymal transition (EMT) and promotes the expression of E-cadherin to prevent cancer cells from leading to the EMT (Cell Cycle 10: 7, 1144-1151 (2011), Cell Cycle 9: 18, 3807-3814 (2010), Cell Cycle 9: 22, 4461-4468 (2010))).

For these reasons, there is need for a biguanide-based substance that exhibits better pharmacological action than conventional metformin and has improved physiochemical properties.

DISCLOSURE OF INVENTION

Technical Problem

The present invention is directed to providing a novel biguanide derivative that is highly effective at inhibiting proliferation of cancer cells, cancer metastasis and cancer recurrence, even when administered in a small dose compared with conventional drugs, or a pharmaceutically acceptable salt thereof, and a method of preparing the same.

Solution to Problem

One aspect of the present invention provides an N1-cyclic amine-N5-substituted biguanide derivative compound represented by the following Formula 1, or a pharmaceutically acceptable salt thereof:

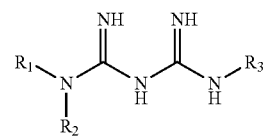

[Formula 1]

In Formula 1, $R_1$ and $R_2$ are taken together with nitrogen to which they are attached to form $C_{3-6}$ heterocycloalkene having 4 to 7 ring atoms; or $C_{3-6}$ heterocycloalkyl having 4 to 7 ring atoms, and $R_3$ is hydrogen; $C_{1-6}$ alkyl; phenyl; or $C_{1-4}$ alkyl substituted with phenyl, wherein the $C_{3-6}$ heterocycloalkene and the $C_{3-6}$ heterocycloalkyl are each independently unsubstituted or substituted with at least one substituent selected from the group consisting of halogen, hydroxy and $C_{1-6}$ alkyl, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

In this specification, a substituted group refers to a group in which at least one hydrogen atom is replaced with at least one non-hydrogen atom group, provided that the group satisfies the valence electron requirements and forms a chemically stable compound from the substitution. Unless explicitly described as unsubstituted in this specification, it should be understood that all substituents will be unsubstituted or substituted with another substituent. The substituents $R_1$ to $R_3$ on the biguanide derivative according to the present invention may each be re-substituted with at least one of the above-defined substituents.

The term halogen or halo- refers to fluoro, chloro, bromo, and iodo.

The term hydroxy refers to —OH.

The term alkyl refers to a linear and branched saturated hydrocarbon group generally having a specified number of carbon atoms (for example, 1 to 12 carbon atoms). Examples of the alkyl group include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl, etc. The alkyl may be attached to a parent group or a substrate at any ring atom, unless the attachment would violate the valence electron requirements. Likewise, the alkyl group may include at least one non-hydrogen substituent unless the substitution would violate the valence electron requirements. For example, the term haloalkyl refers to an alkyl group in which at least one hydrogen atom of the alkyl group is substituted with halogen. For example, when at least one hydrogen atom of methyl group is substituted with halogen, group such as —$CH_2$(halo), —CH(halo)$_2$ or C(halo)$_3$ is formed. Examples of the term haloalkyl group include, without limitation, trifluoromethyl, trichloromethyl, tribromomethyl, and triiodomethyl.

The term alkoxy refers to alkyl-O—, provided that the alkyl is the same as defined above. Examples of the alkoxy group include, without limitation, methoxy, ethoxy, n-propoxy, i-propoxy, n-butoxy, s-butoxy, t-butoxy, n-pentoxy, s-pentoxy, etc. The alkoxy may be attached to a parent group or a substrate at any ring atom, unless the attachment would violate the valence electron requirements. Likewise, the alkoxy group may include at least one non-hydrogen substituent unless the attachment would violate the valence electron requirements. For example, the term haloalkoxy refers to an alkoxy group in which at least one hydrogen atom of the alkoxy group is substituted with halogen. For example, when at least one hydrogen atom of methoxy group is substituted with halogen, group such as —O—$CH_2$(halo), —O—CH(halo)$_2$ or —O—C(halo)$_3$ is formed. Examples of the term haloalkoxy group include, without limitation, trifluoromethoxy, trichloromethoxy, tribromomethoxy, and triiodomethoxy, etc.

The term cycloalkene refers to a saturated monocyclic and polycyclic hydrocarbon ring generally having the specified number of carbon atoms (for example, $C_{3-8}$ cycloalkene refers to cycloalkene group having 3, 4, 5, 6, 7 or 8 carbon atoms as ring members). The cycloalkene may be attached to a parent or substrate at any ring atom, unless the attachment would violate the valence electron requirements. Likewise, the cycloalkene group may include at least one non-hydrogen substituent unless the substitution would violate the valence electron requirements.

The term heterocycloalkene refers to an unsaturated non-aromatic monocyclic and polycyclic hydrocarbon ring in which at least one of ring members in the cycloalkene is composed of elements rather than carbon, including heteroatoms, for example, nitrogen, oxygen or sulfur. The heterocycloalkene may be attached to a parent or substrate at any ring atom, unless the attachment would violate the valence electron requirements. Likewise, the heterocycloalkene group may include at least one non-hydrogen substituent unless the attachment would violate the valence electron requirements. Examples of the heterocycloalkene group include, without limitation, dihydroazetine, dihydropyrrole, dihydropyridine, tetrahydropyridine, dihydroazepine, tetrahydroazepine, etc.

The term cycloalkyl refers to a saturated monocyclic and dicyclic hydrocarbon ring generally having the specified number of carbon atoms included in a ring (that is, $C_{3-8}$ cycloalkyl refers to cycloalkyl group having 3, 4, 5, 6, 7 or 8 carbon atoms as ring members). The cycloalkyl may be attached to a parent or substrate at any ring atom, unless the attachment would violate the valence electron requirements. Likewise, the cycloalkyl group may include at least one non-hydrogen substituent unless the substitution would violate the valence electron requirements.

The term heterocycloalkyl refers to a monocyclic and dicyclic hydrocarbon ring in which at least one of ring system atoms in the cycloalkyl is composed of elements rather than carbon, including heteroatoms, that is, nitrogen, oxygen or sulfur. The heterocycloalkyl may be attached to a parent or substrate at any ring atom, unless the attachment would violate the valence electron requirements. Likewise, the heterocycloalkyl group may include at least one non-hydrogen substituent unless the substitution would violate valence electron requirements. Examples of the heterocycloalkyl group include, without limitation, aziridine, azetidine, imidazolyl, pyrrolyl, pyrrolidinyl, piperidyl, morpholinyl, piperazinyl, azepanyl, indolyl, indolinyl, etc.

According to one exemplary embodiment, $R_1$ and $R_2$ may be taken together with nitrogen to which they are attached to form $C_{4-5}$ heterocycloalkene having 5 to 6 ring atoms or $C_{4-5}$ heterocycloalkyl having 5 to 6 ring atoms, and $R_3$ may be hydrogen; $C_{1-6}$ alkyl; phenyl; or $C_{1-4}$ alkyl substituted with a phenyl, wherein the $C_{4-5}$ heterocycloalkene is unsubstituted or substituted with $C_{1-6}$ alkyl, the $C_{4-5}$ heterocycloalkyl is substituted with 1 to 4 $C_{1-6}$ alkyl groups, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

According to another exemplary embodiment, $R_1$ and $R_2$ may be taken together with nitrogen to which they are attached to form $C_{4-5}$ heterocycloalkene having 5 to 6 ring atoms or $C_{4-5}$ heterocycloalkyl having 5 to 6 ring atoms, $R_3$ may be hydrogen; $C_{1-6}$ alkyl; phenyl; or $C_{1-2}$ alkyl substituted with phenyl, wherein the $C_{4-5}$ heterocycloalkene is unsubstituted or substituted with $C_{1-2}$ alkyl, the $C_{4-5}$ heterocycloalkyl is substituted with one or two $C_{1-2}$ alkyl groups, and the phenyl is unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

According to still another exemplary embodiment, $R_1$ and $R_2$ may be taken together with nitrogen to which they are attached to form $C_{3-6}$ heterocycloalkene selected from the group consisting of dihydroazetinyl; dihydropyrrolinyl; dihydropyridinyl; and tetrahydropyridinyl, or $R_1$ and $R_2$ may be taken together with nitrogen to which they are attached to form $C_{3-6}$ heterocycloalkyl selected from the group consisting of azetidinyl; piperidinyl; and pyrrolidinyl, and $R_3$ may be hydrogen; $C_{1-6}$ alkyl; phenyl; or $C_{1-4}$ alkyl substituted with phenyl, wherein the $C_{3-6}$ heterocycloalkene is unsubstituted or substituted with $C_{1-6}$ alkyl, the $C_{3-6}$ heterocycloalkyl is substituted with 1 to 4 $C_{1-6}$ alkyl groups, and the phenyl is unsubstituted or substituted with at least one non-hydrogen substituent selected from the group consisting of halogen, hydroxy, $C_{1-6}$ alkyl, $C_{1-6}$ alkoxy, $C_{1-6}$ haloalkyl, and $C_{1-6}$ haloalkoxy.

According to still another exemplary embodiment, $R_1$ and $R_2$ may be taken together with nitrogen to which they are attached to form dihydropyrrolinyl or tetrahydropyridinyl which is unsubstituted or substituted with $C_{1-4}$ alkyl, or $R_1$ and $R_2$ may be taken together with nitrogen to which they are attached to form piperidinyl or pyrrolidinyl which is substituted with $C_{1-4}$ alkyl in at least one position thereof, and $R_3$ may be hydrogen; $C_{1-6}$ alkyl; phenyl; or $C_{1-4}$ alkyl substituted with phenyl, wherein the phenyl is unsubstituted or substituted with at least one non-hydrogen substituent selected from the group consisting of halogen, $C_{1-4}$ alkoxy, $C_{1-4}$ haloalkyl, and $C_{1-4}$ haloalkoxy.

According to still another exemplary embodiment, $R_1$ and $R_2$ may be taken together with nitrogen to which they are attached to form dihydropyrrolinyl or tetrahydropyridinyl which is unsubstituted or substituted with $C_{1-2}$ alkyl, or $R_1$ and $R_2$ may be taken together with nitrogen to which they are attached to form piperidinyl or pyrrolidinyl substituted with one or two $C_{1-2}$ alkyl groups, and $R_3$ may be hydrogen; $C_{3-6}$ alkyl; phenyl; or $C_{1-2}$ alkyl substituted with phenyl, wherein the phenyl is unsubstituted or substituted with at least one non-hydrogen substituent selected from the group consisting of halogen, $C_{1-2}$ alkoxy, $C_{1-2}$ haloalkyl, and $C_{1-2}$ haloalkoxy.

According to yet another exemplary embodiment, $R_1$ and $R_2$ may be taken together with nitrogen to which they are attached to form dihydropyrrolinyl or tetrahydropyridinyl which is unsubstituted or substituted with methyl, or $R_1$ and $R_2$ may be taken together with nitrogen to which they are attached to form piperidine, and $R_3$ may be hydrogen; butyl; propyl; hexyl; phenyl; or methyl substituted with phenyl, wherein the piperidine is substituted with one or two methyl groups in at least one of positions 2, 3, 5 and 6, and the phenyl is unsubstituted or substituted with at least one non-hydrogen substituent selected from the group consisting of halogen, methoxy, trihalomethyl, and trihalomethoxy.

According to one exemplary embodiment, the compound of Formula 1 may include

N1-1,2-dihydropyrrole-N5-(4-trifluoromethoxy)phenyl biguanide;
N1-1,2-dihydropyrrole-N5-(4-trifluoromethyl)phenyl biguanide;
N1-1,2-dihydropyrrole-N5-(3-trifluoromethyl)phenyl biguanide;
N1-1,2-dihydropyrrole-N5-(4-fluoro)phenyl biguanide;
N1-1,2-dihydropyrrole-N5-(4-chloro)phenyl biguanide;
N1-1,2-dihydropyrrole-N5-(4-bromo)phenyl biguanide;
N1-1,2-dihydropyrrole-N5-(3-chloro, 4-trifluoromethoxy)phenyl biguanide;
N1-1,2,3,6-tetrahydropyridine-N5-(3-chloro, 4-trifluoromethoxy)phenyl biguanide;
N1-1,2-dihydropyrrole-N5-(3-trifluoromethyl)benzyl biguanide;
N1-1,2-dihydropyrrole-N5-(4-trifluoromethyl)benzyl biguanide;
N1-1,2-dihydropyrrole-N5-(3-trifluoromethoxy)benzyl biguanide;
N1-(3-methyl)-1,2-dihydropyrrole-N5-(4-trifluoromethoxy)phenyl biguanide;
N1-(3-methyl)-1,2-dihydropyrrole-N5-(4-trifluoromethyl)phenyl biguanide;
N1-(3-methyl)-1,2-dihydropyrrole-N5-(4-chloro)phenyl biguanide;
N1-(3-methyl)-1,2-dihydropyrrole-N5-(4-chloro, 3-trifluoromethyl)phenyl biguanide;
N1-(3-methyl)-1,2-dihydropyrrole-N5-(3-trifluoromethyl)phenyl biguanide;
N1-(3-methyl)-1,2-dihydropyrrole-N5-(4-fluoro)phenyl biguanide;
N1-(3-methyl)-1,2-dihydropyrrole-N5-(4-bromo)phenyl biguanide;
N1-(3-methyl)-1,2-dihydropyrrole-N5-(4-methoxy)phenyl biguanide;
N1-(3-methyl)-1,2-dihydropyrrole-N5-(3,4-dimethoxy)phenyl biguanide;
N1-(3-methyl)-1,2-dihydropyrrole-N5-(4-trifluoromethoxy)benzyl biguanide;
N1-(3-methyl)-1,2-dihydropyrrole-N5-(3-trifluoromethoxy)phenyl biguanide;
N1-(3-methyl)-1,2-dihydropyrrole-N5-(4-trifluoromethyl)benzyl biguanide;
N1-(3-methyl)-1,2-dihydropyrrole-N5-(4-chloro, 3-trifluoromethyl)benzyl biguanide;
N1-1,2,3,6-tetrahydropyridine-N5-(4-trifluoromethoxy)phenyl biguanide;
N1-1,2,3,6-tetrahydropyridine-N5-(4-trifluoromethyl)phenyl biguanide;
N1-1,2,3,6-tetrahydropyridine-N5-(3-trifluoromethoxy)phenyl biguanide;
N1-1,2,3,6-tetrahydropyridine-N5-(3-trifluoromethyl)phenyl biguanide;
N1-1,2,3,6-tetrahydropyridine-N5-(4-fluoro, 3-trifluoromethyl)phenyl biguanide;
N1-1,2,3,6-tetrahydropyridine-N5-(4-chloro, 3-trifluoromethoxy)phenyl biguanide;
N1-1,2,3,6-tetrahydropyridine-N5-(3-fluoromethoxy)phenyl biguanide;
N1-1,2,3,6-tetrahydropyridine-N5-(4-chloro)phenyl biguanide;
N1-1,2,3,6-tetrahydropyridine-N5-(4-bromo)phenyl biguanide;
N1-1,2,3,6-tetrahydropyridine-N5-(4-fluoro)phenyl biguanide;
N1-1,2,3,6-tetrahydropyridine-N5-(3,5-dimethoxy)phenyl biguanide;
N1-1,2,3,6-tetrahydropyridine-N5-(4-methoxy)phenyl biguanide;
N1-1,2,3,6-tetrahydropyridine-N5-(3-methoxy)phenyl biguanide;
N1-1,2-dihydropyrrole-N5-(4-methoxy)phenyl biguanide;
N1-1,2-dihydropyrrole-N5-(3-methoxy)phenyl biguanide;
N1-1,2-dihydropyrrole-N5-phenyl biguanide;
N1-1,2-dihydropyrrole-N5-(3,5-dimethoxy)phenyl biguanide;
N1-1,2-dihydropyrrole-N5-(4-fluoro, 3-trifluoromethyl)phenyl biguanide;
N1-1,2-dihydropyrrole-N5-(3-fluoro, 4-trifluoromethyl)phenyl biguanide;
N1-1,2,3,6-tetrahydropyridine-N5-(4-methyl)phenyl biguanide;
N1-1,2,3,6-tetrahydropyridine-N5-(3-methyl)phenyl biguanide;
N1-1,2-dihydropyrrole-N5-(4-methyl)phenyl biguanide;
N1-1,2-dihydropyrrole-N5-(3-methyl)phenyl biguanide;
N1-1,2-dihydropyrrole-N5-(3-trifluoromethoxy)phenyl biguanide;
N1-1,2,3,6-tetrahydropyridine-N5-hexyl biguanide;
N1-1,2,3,6-tetrahydropyridine-N5-(4-trifluoromethoxy)benzyl biguanide;

N1-1,2,3,6-tetrahydropyridine-N5-(3-trifluoromethoxy) benzyl biguanide;
N1-1,2,3,6-tetrahydropyridine-N5-(4-trifluoromethyl)benzyl biguanide;
N1-1,2,3,6-tetrahydropyridine-N5-(3-trifluoromethyl)benzyl biguanide;
N1-1,2,3,6-tetrahydropyridine-N5-(4-chloro, 3-trifluoromethyl)benzyl biguanide;
N1-1,2,3,6-tetrahydropyridine-N5-butyl biguanide;
N1-1,2,3,6-tetrahydropyridine-N5-propyl biguanide; N1-1,2,3,6-tetrahydropyridine biguanide; N1-(3-methyl)piperidine-N5-(3-trifluoromethyl)benzyl biguanide;
N1-(3-methyl)piperidine-N5-(4-chloro)benzyl biguanide;
N1-(3-methyl)piperidine-N5-(4-fluoro)phenyl biguanide;
N1-(3-methyl)piperidine-N5-(4-bromo)phenyl biguanide;
N1-(3-methyl)piperidine-N5-(4-chloro, 3-trifluoromethyl)phenyl biguanide;
N1-(3-methyl)piperidine-N5-(3-fluoro, 4-trifluoromethyl)phenyl biguanide;
N1-(3-methyl)piperidine-N5-(4-fluoro, 3-trifluoromethyl)phenyl biguanide;
N1-(2-methyl)piperidine-N5-(4-trifluoromethoxy)phenyl biguanide;
N1-(2-methyl)piperidine-N5-(3-trifluoromethoxy)phenyl biguanide;
N1-(2-methyl)piperidine-N5-(4-trifluoromethyl)phenyl biguanide;
N1-(3-methyl)piperidine-N5-(3-fluoro, 4-trifluoromethoxy)phenyl biguanide;
N1-(2-methyl)piperidine-N5-(3-fluoro, 4-trifluoromethoxy)phenyl biguanide;
N1-(2-methyl)piperidine-N5-(4-chloro)phenyl biguanide;
N1-(2-methyl)piperidine-N5-(4-fluoro, 3-trifluoromethyl)phenyl biguanide;
N1-(2-methyl)piperidine-N5-(3-trifluoromethyl)phenyl biguanide;
N1-(2-methyl)piperidine-N5-(4-chloro, 3-trifluoromethyl)phenyl biguanide;
N1-(3-methyl)piperidine-N5-(4-trifluoromethyl)phenyl biguanide;
N1-(3-methyl)piperidine-N5-(4-trifluoromethoxy)phenyl biguanide;
N1-(3-methyl)piperidine-N5-(3-trifluoromethoxy)phenyl biguanide;
N1-(3-methyl)piperidine-N5-(4-trifluoromethoxy)benzyl biguanide;
N1-(3-methyl)piperidine-N5-(4-fluoro, 3-trifluoromethyl)phenyl biguanide;
N1-(3-methyl)piperidine-N5-(4-trifluoromethyl)benzyl biguanide;
N1-(3-methyl)piperidine-N5-(4-chloro)phenyl biguanide;
N1-(3-methyl)piperidine-N5-(3-trifluoromethyl)phenyl biguanide;
N1-(2,6-dimethyl)piperidine-N5-(4-trifluoromethoxy)phenyl biguanide;
N1-(2,6-dimethyl)piperidine-N5-(3-trifluoromethoxy)phenyl biguanide;
N1-(2,6-dimethyl)piperidine-N5-(4-trifluoromethyl)phenyl biguanide;
N1-(2,6-dimethyl)piperidine-N5-(3-trifluoromethyl)phenyl biguanide;
N1-(2,6-dimethyl)piperidine-N5-(4-fluoro, 3-trifluoromethyl)phenyl biguanide;
N1-(2,6-dimethyl)piperidine-N5-(4-chloro, 3-trifluoromethyl)phenyl biguanide;
N1-(2,6-dimethyl)piperidine-N5-(3-fluoro, 4-trifluoromethoxy)phenyl biguanide;
N1-(2,6-dimethyl)piperidine-N5-(4-chloro)phenyl biguanide;
N1-(2,6-dimethyl)piperidine-N5-(4-bromo)phenyl biguanide; or
N1-(2,6-dimethyl)piperidine-N5-(4-fluoro)phenyl biguanide.

Meanwhile, a pharmaceutically acceptable salt of the compound of Formula 1 according to the present invention may be an acid addition salt formed using an organic acid or an inorganic acid. For example, the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxy acetic acid, benzenesulfonic acid, 4-toluenesulfonic acid and methanesulfonic acid; and the inorganic acid may include, for example, hydrochloric acid, hydrobromic acid, sulfuric acid, phosphoric acid, nitric acid, carbonic acid and boric acid. For example, the above-described acid addition salt may be prepared by a typical method of preparing a salt, including a) directly mixing the compound of Formula 1 and an acid, b) dissolving one of the compound and an acid in a solvent or a hydrated solvent and mixing the resulting solution, or c) mixing the compound of Formula 1 and the acid in the presence of a solvent or a hydrated solvent.

According to one exemplary embodiment, the pharmaceutically acceptable salt of the compound represented by Formula 1 may be a salt of an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid, and boric acid.

The compound of Formula 1 according to the present invention may be prepared by several methods.

According to one exemplary embodiment, there is provided a method of preparing a compound represented by the following Formula 1, which includes reacting a compound of the following Formula 2 with a dicyanamide in an organic solvent to obtain a compound of the following Formula 3; and reacting the compound of the following Formula 3 with a compound of the following Formula 4 in an organic solvent to obtain the compound of the following Formula 1:

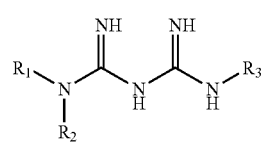

[Formula 1]

[Formula 2]

-continued

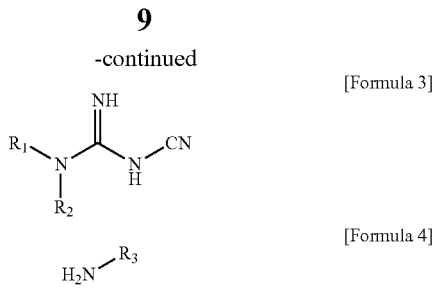

In Formulas 1 to 4, $R_1$, $R_2$ and $R_3$ are the same as defined in Formula 1.

For example, the preparation method may be illustrated in the following Scheme 1, and will be described by operations, as follows.

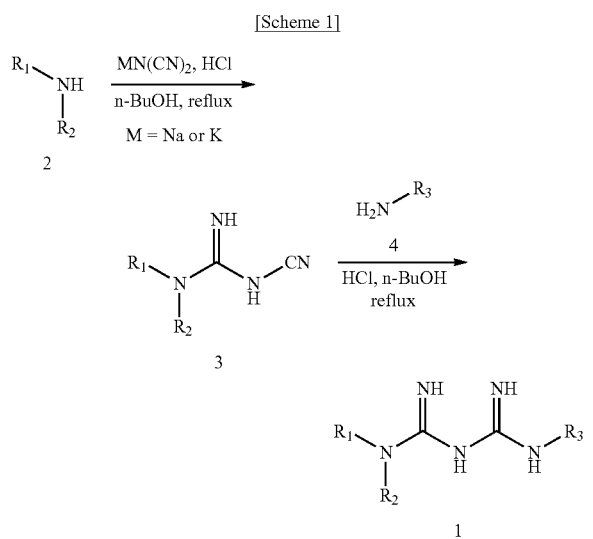

In the method of preparing the compound of Formula 1, the cyanoguanidine compound of Formula 3 used as an intermediate may be obtained by reacting the cyclic amine of Formula 2 with a dicyanamide such as sodium or potassium dicyanamide in an organic solvent in the presence of an acid. Then, the compound of Formula 1 may be obtained by refluxing the obtained cyanoguanidine compound of Formula 3 with the compound of Formula 4 in an organic solvent.

An amount of the dicyanamide used for preparation of the cyanoguanidine compound of Formula 3 is equivalent to approximately 1 to 3 moles with respect to the compound of Formula 2, and an amount of the acid used is equivalent to approximately 1 to 2 moles with respect to the compound of Formula 2. Upon preparation of the compound of Formula 2, methanol, ethanol, propanol, butanol, pentanol, acetonitrile, benzene, toluene, 1,4-dioxane, N,N-dimethylamide, and the like may be, for example, used as the organic solvent, and hydrochloric acid, sulfuric acid, nitric acid, hydrobromic acid, 4-toluenesulfonic acid, and the like may be, used as the acid. The reaction temperature of the compound of Formula 2 and the dicyanamide may be in a range of 60 to 140° C., and the reaction time may be in a range of 3 to 24 hours.

After the cyanoguanidine compound of Formula 3 obtained above is dissolved in an organic solvent, the compound of Formula 4 and an acid are added, and then stirred under reflux. In this case, an amount of the compound of Formula 4 is equivalent to approximately 1 to 2 moles with respect to the compound of Formula 3, and an amount of the acid is equivalent to approximately 1 to 2 moles with respect to the compound of Formula 3. For example, the organic solvent used in reaction of the compound of Formula 3 and the compound of Formula 4 may include methanol, ethanol, propanol, butanol, pentanol, acetonitrile, benzene, toluene, 1,4-dioxane, N,N-dimethylamide, and the like, and the acid may, for example, include hydrochloric acid, sulfuric acid, nitric acid, hydrobromic acid, 4-toluenesulfonic acid, and the like. In this case, the reaction temperature may be in a range of a reflux temperature of the solvent used (i.e., 120 to 140° C. for butanol), and the reaction time may be in a range of 6 to 24 hours. When the reaction is completed, the resulting reaction solution is filtered. Thereafter, a pH of the filtered reaction solution may be controlled to approximately 4 to 5 using an acid such as, hydrochloric acid. Then, the resulting reaction solution may be concentrated and purified to yield the compound of Formula 1 or a pharmaceutically acceptable salt thereof according to the present invention.

The compound of Formula 1 or the pharmaceutically acceptable salt thereof produced in this way may be useful in performing anticancer treatment including inhibition of cancer metastasis and cancer recurrence by AMPK activation, even when administered in a small dose compared with conventional drugs, as will be confirmed in the following Examples.

Therefore, the present invention provides a medicine including the compound of Formula 1 or the pharmaceutically acceptable salt thereof as an active ingredient.

Another aspect of the present invention provides a pharmaceutical composition for preventing or treating a cancer, which includes the compound of Formula 1 or the pharmaceutically acceptable salt thereof as an active ingredient, the use of the compound of Formula 1 or the pharmaceutically acceptable salt thereof to prepare a medicine for preventing or treating the disease, and a method of preventing or treating the disease including administering a therapeutically effective amount of the compound of Formula 1 or the pharmaceutically acceptable salt thereof to a subject.

The pharmaceutical composition of the present invention includes at least one pharmaceutically acceptable carrier in addition to the active ingredient. As used in this specification, the term pharmaceutically acceptable carrier refers to a known pharmaceutically acceptable excipient, which is useful to formulate a pharmaceutically active compound for administration, and is substantially non-toxic and non-sensitive under the conditions used. An exact ratio of the excipient is determined by standard pharmaceutical practice, as well as solubility, chemical characteristics and selected route for administration of the active compound.

The pharmaceutical composition of the present invention may be formulated in a form suitable for a desired administration method using a suitable and physiologically available adjuvant such as an excipient, a disintegrating agent, a sweetening agent, a binder, a coating agent, a swelling agent, a lubricating agent, a glossing agent, a flavoring agent, or the like.

The pharmaceutical composition may be formulated as a tablet, a capsule, a pill, a granule, a powder, an injection or a liquid, but the present invention is not limited thereto.

The formulation and the pharmaceutically acceptable carrier of the pharmaceutical composition may be properly selected according to the techniques known in the related art, and, for example, may be selected with reference to the following documents: (Urquhart et al., Lancet, 16:367, 1980); (Lieberman et al., PHARMACEUTICAL DOSAGE FORMS-DISPERSE SYSTEMS, 2nd ed., vol. 3, 1998); (Ansel et al., PHARMACEUTICAL DOSAGE FORMS & DRUG DELIVERY SYSTEMS, 7th ed., 2000); (Martindale, THE EXTRA PHARMACOPEIA, 31st ed.); (Remington's PHARMACEUTICAL SCIENCES, 16th-20th editions); (THE PHARMACOLOGICAL BASIS OF THERAPEUTICS, Goodman and Gilman, eds., 9th ed., 1996); and (Wilson and Gisvolds' TEXTBOOK OF ORGANIC MEDICINAL AND PHARMACEUTICAL CHEMISTRY, Delgado and Remers, eds., 10th ed., 1998). Also, principals of formulating a pharmaceutical composition may be described, for example, with reference to the following documents: (Platt, Clin Lab Med, 7:289-99, 1987); (Aulton, PHARMACEUTICS: THE SCIENCE OF DOSAGE FORM DESIGN, Churchill Livingstone, N Y, 1988); (EXTEMPORANEOUS ORAL LIQUID DOSAGE PREPARATIONS, CSHP, 1998); and (Drug Dosage, J Kans Med Soc, 70(1): 30-32, 1969).

According to one exemplary embodiment, the pharmaceutical composition may be used together with a second drug.

According to the present invention, the term second drug refers to another pharmaceutically active ingredient in addition to the biguanide derivative according to the present invention. The compound of Formula 1 or the pharmaceutically acceptable salt thereof according to the present invention may be used to treat a variety of diseases, as described above. As a result, the compound of Formula 1 or the pharmaceutically acceptable salt thereof according to the present invention may be used together with a second drug for effectively treating respective diseases. For example, the second drug may be an anticancer agent, an anti-hyperglycemic agent, an anti-obesity agent, etc., which includes an active ingredient different from the compound of Formula 1 or the pharmaceutically acceptable salt thereof.

When the compound of Formula 1 or the pharmaceutically acceptable salt thereof according to the present invention and the second drug are able to be administered in the same manner, the compound of Formula 1 or the pharmaceutically acceptable salt thereof may be formulated together with the second drug to be provided in the form of a composite preparation.

Meanwhile, according to the present invention, the term subject refers to a warm-blooded animal such as a mammal with a specific condition, disorder or disease. For example, the subject may be a human, an orangutan, a chimpanzee, a mouse, a rat, a dog, a cow, a chicken, a pig, a goat, a sheep, etc., but the present invention is not limited thereto.

Also, the term treating includes relieving a symptom, temporarily or permanently eliminating causes of the symptom, and preventing or hindering occurrence of the symptom or progression of the above-described condition, disorder or disease, but the present invention is not limited thereto.

An effective amount of the active ingredient of the pharmaceutical composition according to the present invention refers to an amount required to treat a disease. Therefore, the effective amount of the active ingredient may be adjusted according to various factors such as kinds and severity of a disease, kinds and contents of an active ingredient and other ingredients included in the composition, kinds of a formulation, age, body weight, general medical conditions, sex and diet of a patient, duration and route of administration, a release rate of the composition, treatment duration, and the number of drugs used together. In the case of adults, for example, the compound of Formula 1 may be administered in a total dose of 50 to 3,000 mg/kg when administered once to several times a day.

Advantageous Effects of Invention

The N1-cyclic amine-N5-substituted biguanide derivative of Formula 1 according to the present invention can be highly useful in treating a cancer since the N1-cyclic amine-N5-substituted biguanide derivative of Formula 1 has an effect of inhibiting cancer cell proliferation, cancer metastasis and recurrence even when administered in a small dose compared with conventional drugs.

MODE FOR THE INVENTION

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1: Synthesis of N1-2,5-dihydropyrrole cyanoguanidine

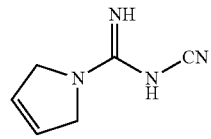

2,5-Dihydropyrrole hydrochloride (0.75 g, 7.104 mmol) and sodium dicyanamide (0.63 g, 7.104 mmol) were dissolved in a butanol (20 mL) solution, and then stirred for 3 hours under reflux. After completion of the reaction was confirmed, sodium chloride formed by filtering the reaction mixture was removed, and the filtrate was then concentrated at a reduced pressure. The concentrate was dissolved in methanol (2 mL), and ethyl acetate (5 mL) was then added thereto, and stirred at room temperature for an hour. The formed solid was filtered and the filtrate was washed with ethyl acetate (2×20 mL). The filtrate was dried at a reduced pressure to obtain a white solid target compound (0.90 g, 93%).

$^1$H NMR (600 MHz, CD$_3$OD) δ 5.89 (m, 2H), 4.16 (m, 4H); LC-MS m/z 137.2 [M+1]$^+$

Example 2: Synthesis of N1-1,2,3,6-tetrahydropyridine cyanoguanidine

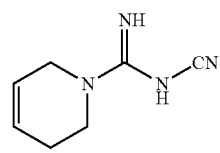 [SMILES: N#CNC(=N)N1CC=CCC1]

A white solid target compound (2.23 g, 59.2%) was prepared in the same manner as in Example 1, except that 1,2,3,6-tetrahydropyridine was used instead of the 2,5-dihydropyrrole hydrochloride used in Example 1.

$^1$H NMR (600 MHz, CD$_3$OD) δ 5.90 (d, 1H), 5.69 (d, 1H), 3.93 (t, 2H), 3.59 (t, 2H), 2.18 (m, 2H); LC-MS m/z 151.2 [M+1]$^+$

Example 3: Synthesis of
N1-3-methyl-2,5-dihydropyrrole cyanoguanidine

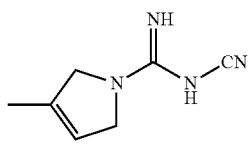

A white solid target compound (3.12 g, 83%) was prepared in the same manner as in Example 1, except that 3-methyl-2,5-dihydropyrrole was used instead of the 2,5-dihydropyrrole hydrochloride used in Example 1.

$^1$H NMR (600 MHz, CD$_3$OD) δ 5.45 (br s, 1H), 4.80 (m, 2H), 4.10 (m, 2H) 7.16 (s, 3H); LC-MS m/z 151.2 [M+1]$^+$

Example 4: Preparation of N1-1,2-dihydropyrrole-N5-(4-trifluoromethoxy)phenyl biguanide hydrochloride

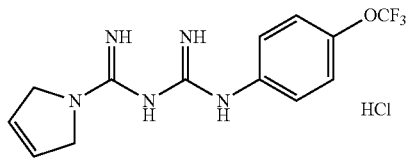 [SMILES: N=C(NC(=N)N1CC=CC1)Nc1ccc(OC(F)(F)F)cc1 ; Cl]

(4-Trifluoromethoxy)phenylamine (390 mg, 2.20 mmol) was dissolved in a butanol (10 mL) solution at room temperature, and concentrated hydrochloric acid (0.18 mL, 2.20 mmol) was added to the resulting solution, and then stirred for 30 minutes. The N1-2,5-dihydropyrrole cyanoguanidine (300 mg, 2.20 mmol) obtained in Example 1 was added to the reaction mixture, and then stirred for an hour under reflux. The reaction mixture was stirred at room temperature for an hour, and the formed solid was filtered. Then, the filtrate was dried at a reduced pressure to obtain a white solid target compound (265 mg, 34%).

$^1$H NMR (600 MHz, CD$_3$OD) δ 3.94 (m, 2H), 3.71 (m, 2H), 3.47 (m, 1H), 3.34 (s, 3H), 2.90 (m, 1H), 2.57 (m, 1H), 1.71 (m, 10H), 1.18 (m, 1H), 0.89 (s, 3H); LC-MS m/z 282.2 [M+1]$^+$; mp 172-174° C.

Target compounds of the following Examples 5 to 61 were prepared in the same manner as in Example 4, except that the cyanoguanidine and amine compounds synthesized in Examples 2 and 3, which corresponded to the target compounds, were used respectively instead of the N1-2,5-dihydropyrrole cyanoguanidine synthesized in Example 1 and the (4-trifluoromethoxy)phenylamine used in Example 4.

Example 5: Preparation of
N1-1,2-dihydropyrrole-N5-(4-trifluoromethyl)phenyl biguanide hydrochloride

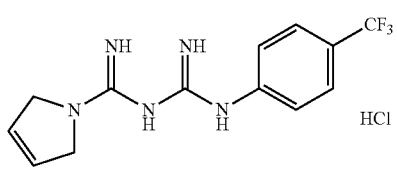 [SMILES: N=C(NC(=N)N1CC=CC1)Nc1ccc(C(F)(F)F)cc1 ; Cl]

$^1$H NMR (600 MHz, CD$_3$OD) δ 7.58 (m, 4H), 5.91 (m, 2H), 4.27 (m, 4H); LC-MS m/z 298.2 [M+1]$^+$; mp 254-256° C.

Example 6: Preparation of
N1-1,2-dihydropyrrole-N5-(3-trifluoromethyl)phenyl biguanide hydrochloride

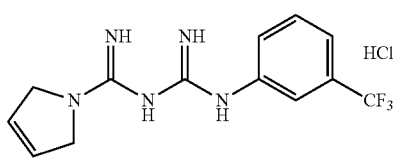 [SMILES: N=C(NC(=N)N1CC=CC1)Nc1cccc(C(F)(F)F)c1 ; Cl]

$^1$H NMR (600 MHz, CD$_3$OD) δ 7.79 (m, 1H), 7.56 (m, 1H), 7.46 (m, 1H), 7.34 (m, 1H), 5.91 (s, 2H), 4.20 (m, 4H); LC-MS m/z 298.2 [M+1]$^+$; mp 276-278° C.

Example 7: Preparation of
N1-1,2-dihydropyrrole-N5-(4-fluoro)phenyl biguanide hydrochloride

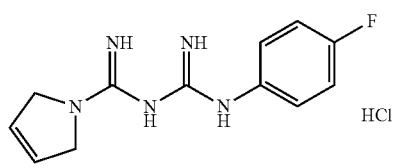 [SMILES: N=C(NC(=N)N1CC=CC1)Nc1ccc(Cl)cc1 ; Cl]

$^1$H NMR (600 MHz, CD$_3$OD) δ 7.33 (m, 2H), 7.04 (m, 2H), 5.90 (m, 2H), 4.17 (m, 4H); LC-MS m/z 248.2 [M+1]$^+$; mp 263-265° C.

Example 8:
N1-1,2-dihydropyrrole-N5-(4-chloro)phenyl biguanide hydrochloride

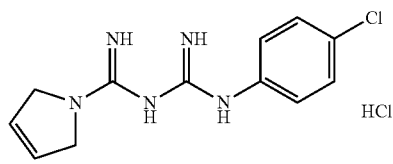

¹H NMR (600 MHz, CD₃OD) δ 7.29 (m, 4H), 5.90 (m, 2H), 4.20 (m, 4H); LC-MS m/z 264.2 [M+1]⁺; mp 264-266° C.

Example 9:
N1-1,2-dihydropyrrole-N5-(4-bromo)phenyl biguanide hydrochloride

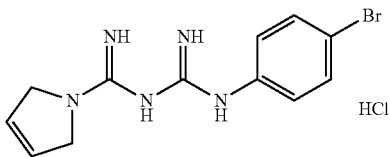 [SMILES: N=C(NC(=N)N1CC=CC1)Nc1ccc(Br)cc1 ; Cl]

¹H NMR (600 MHz, CD₃OD) δ 7.42 (m, 2H), 7.30 (m, 2H), 5.90 (m, 2H), 4.24 (m, 4H); LC-MS m/z 309.0 [M+1]⁺; mp 263-265° C.

Example 10: N1-1,2-dihydropyrrole-N5-(3-chloro,4-trifluoromethoxy)phenyl biguanide hydrochloride

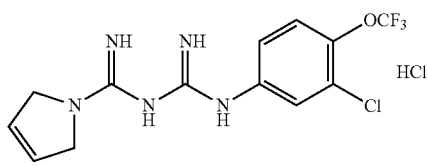 [SMILES: N=C(NC(=N)N1CC=CC1)Nc1ccc(OC(F)(F)F)c(Cl)c1 ; Cl]

¹H NMR (600 MHz, CD₃OD) δ 7.79 (m, 1H), 7.42 (m, 2H), 5.99 (m, 2H), 4.30 (m, 4H); LC-MS m/z 348.2 [M+1]⁺; mp 270-272° C.

Example 11: N1-1,2,3,6-tetrahydropyridine-N5-(3-chloro,4-trifluoromethoxy) phenyl biguanide hydrochloride

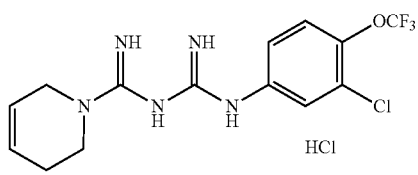 [SMILES: N=C(NC(=N)N1CC=CCC1)Nc1ccc(OC(F)(F)F)c(Cl)c1 ; Cl]

¹H NMR (600 MHz, CD₃OD) δ 7.70 (m, 1H), 7.33 (m, 2H), 5.94 (m, 1H), 5.73 (m, 1H), 3.99 (m, 2H), 3.63 (m, 2H), 2.23 (m, 2H); LC-MS m/z 362.2 [M+1]⁺; mp 250-252° C.

Example 12:
N1-1,2-dihydropyrrole-N5-(3-trifluoromethyl)benzyl biguanide hydrochloride

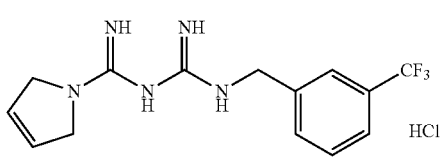 [SMILES: N=C(NCc1cccc(C(F)(F)F)c1)NC(=N)N1CC=CC1 ; Cl]

¹H NMR (600 MHz, CD₃OD) δ 7.70 (m, 4H), 5.89 (m, 2H), 4.52 (m, 2H), 4.23 (m, 4H); LC-MS m/z 312.2 [M+1]⁺; mp 156-158° C.

Example 13:
N1-1,2-dihydropyrrole-N5-(4-trifluoromethyl)benzyl biguanide hydrochloride

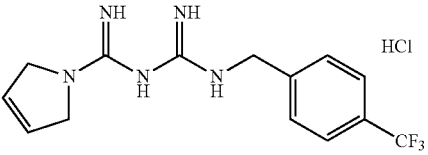 [SMILES: N=C(NCc1ccc(C(F)(F)F)cc1)NC(=N)N1CC=CC1 ; Cl]

¹H NMR (600 MHz, CD₃OD) δ 7.45 (m, 2H), 7.62 (m, 2H), 5.86 (m, 2H), 4.19 (m, 2H), 4.13 (m, 4H); LC-MS m/z 312.2 [M+1]⁺; mp 268-270° C.

Example 14: N1-1,2-dihydropyrrole-N5-(3-trifluoromethoxy)benzyl biguanide hydrochloride

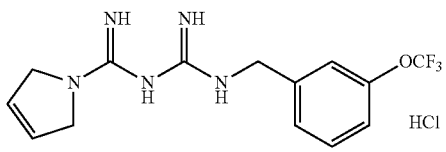 [SMILES: N=C(NCc1cccc(OC(F)(F)F)c1)NC(=N)N1CC=CC1 ; Cl]

¹H NMR (600 MHz, CD₃OD) δ 7.33 (m, 4H), 5.88 (m, 2H), 4.47 (s, 2H), 4.18 (m, 4H); LC-MS m/z 328.2 [M+1]⁺; mp 218-220° C.

Example 15: N1-(3-methyl)-1,2-dihydropyrrole-N5-(4-trifluoromethoxy)phenyl biguanide hydrochloride

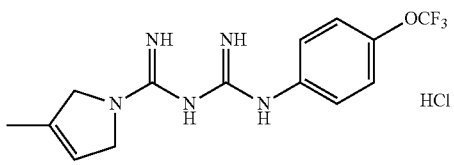 [SMILES: CC1=CCN(C(=N)NC(=N)Nc2ccc(OC(F)(F)F)cc2)C1 ; Cl]

¹H NMR (600 MHz, CD₃OD) δ 7.41 (m, 2H), 7.16 (m, 2H), 5.46 (m, 1H), 4.10 (m, 3H), 1.77 (m, 3H); LC-MS m/z 328.2 [M+1]⁺; mp 279-281° C.

Example 16: N1-(3-methyl)-1,2-dihydropyrrole-N5-(4-trifluoromethyl)phenyl biguanide hydrochloride

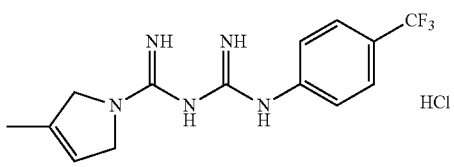 [SMILES: CC1=CCN(C(=N)NC(=N)Nc2ccc(C(F)(F)F)cc2)C1 ; Cl]

¹H NMR (600 MHz, CD₃OD) δ 7.62 (m, 4H), 5.56 (m, 1H), 4.21 (m, 4H), 1.87 (m, 3H); LC-MS m/z 312.2 [M+1]⁺; mp 272-274° C.

Example 17: N1-(3-methyl)-1,2-dihydropyrrole-N5-(4-chloro)phenyl biguanide hydrochloride

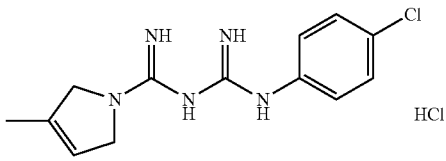 [SMILES: CC1=CCN(C(=N)NC(=N)Nc2ccc(Cl)cc2)C1 ; Cl]

¹H NMR (600 MHz, CD₃OD) δ 7.36 (m, 2H), 7.29 (m, 2H), 5.50 (m, 1H), 4.13 (m, 4H), 1.80 (m, 3H); LC-MS m/z 278.2 [M+1]⁺; mp 264-268° C.

Example 18: N1-(3-methyl)-1,2-dihydropyrrole-N5-(4-chloro, 3-trifluoromethyl)phenyl biguanide hydrochloride

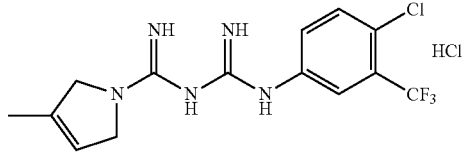 [SMILES: CC1=CCN(C(=N)NC(=N)Nc2ccc(Cl)c(C(F)(F)F)c2)C1 ; Cl]

¹H NMR (600 MHz, CD₃OD) δ 7.92 (m, 1H), 7.58 (m, 1H), 7.50 (m, 1H), 5.51 (s, 1H), 4.17 (m, 4H), 1.82 (m, 3H); LC-MS m/z 346.2 [M+1]⁺; mp 274-276° C.

Example 19: N1-(3-methyl)-1,2-dihydropyrrole-N5-(3-trifluoromethyl)phenyl biguanide hydrochloride

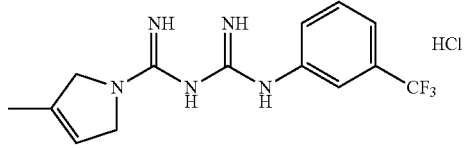 [SMILES: CC1=CCN(C(=N)NC(=N)Nc2cccc(C(F)(F)F)c2)C1 ; Cl]

¹H NMR (600 MHz, CD₃OD) δ 7.80 (m, 1H), 7.57 (m, 1H), 7.42 (m, 1H), 7.34 (m, 1H), 5.51 (m, 1H), 4.15 (m, 4H), 1.81 (m, 3H); LC-MS m/z 312.2 [M+1]⁺; mp 282-284° C.

Example 20: N1-(3-methyl)-1,2-dihydropyrrole-N5-(4-fluoro)phenyl biguanide hydrochloride

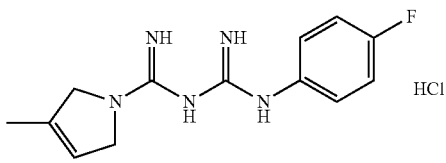 [SMILES: CC1=CCN(C(=N)NC(=N)Nc2ccc(F)cc2)C1 ; Cl]

¹H NMR (600 MHz, CD₃OD) δ 7.34 (m, 2H), 7.04 (m, 2H), 5.50 (m, 1H), 4.12 (m, 4H), 1.80 (m, 3H); LC-MS m/z 262.1 [M+1]⁺; mp 270-272° C.

Example 21: N1-(3-methyl)-1,2-dihydropyrrole-N5-(4-bromo)phenyl biguanide hydrochloride

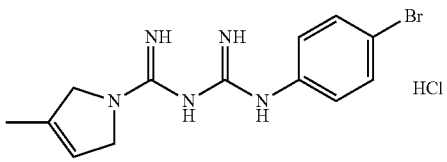

¹H NMR (600 MHz, CD₃OD) δ 7.45 (m, 2H), 7.33 (m, 2H), 5.52 (m, 1H), 4.16 (m, 4H), 1.83 (m, 3H); LC-MS m/z 323.0 [M+1]+; mp 272-274° C.

Example 22: N1-(3-methyl)-1,2-dihydropyrrole-N5-(4-methoxy)phenyl biguanide hydrochloride

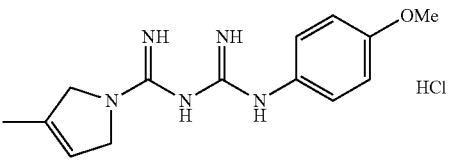 [SMILES: COc1ccc(NC(=N)NC(=N)N2CC=C(C)C2)cc1 ; Cl]

¹H NMR (600 MHz, CD₃OD) δ 7.24 (m, 2H), 6.87 (m, 2H), 5.48 (s, 1H), 3.32 (s, 3H), 1.78 (m, 3H); LC-MS m/z 274.2 [M+1]⁺; mp 263-265° C.

Example 23: N1-(3-methyl)-1,2-dihydropyrrole-N5-(3,4-dimethoxy)phenyl biguanide hydrochloride

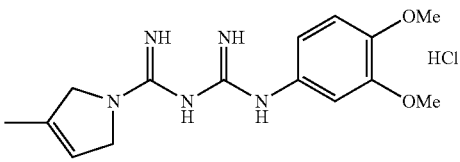 [SMILES: COc1ccc(NC(=N)NC(=N)N2CC=C(C)C2)cc1OC ; Cl]

¹H NMR (600 MHz, CD₃OD) δ 6.58 (m, 2H), 6.26 (m, 1H), 5.52 (m, 1H), 4.18 (m, 4H), 3.30 (s, 3H), 1.83 (m, 3H); LC-MS m/z 304.2 [M+1]⁺; mp 261-263° C.

Example 24: N1-(3-methyl)-1,2-dihydropyrrole-N5-(4-trifluoromethoxy)benzyl biguanide hydrochloride

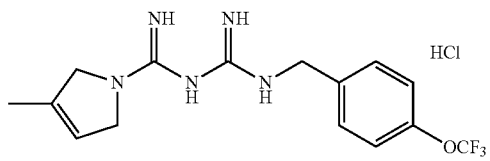 [SMILES: CC1=CCN(C(=N)NC(=N)NCc2ccc(OC(F)(F)F)cc2)C1 ; Cl]

¹H NMR (600 MHz, CD₃OD) δ 7.59 (m, 1H), 7.43 (m, 2H), 7.35 (m, 1H), 7.25 (m, 1H), 5.46 (m, 1H), 4.43 (m, 2H), 4.15 (m, 2H), 1.81 (m, 3H); LC-MS m/z 342.2 [M+1]⁺; mp 184-186° C.

Example 25: N1-(3-methyl)-1,2-dihydropyrrole-N5-(3-trifluoromethoxy)phenyl biguanide hydrochloride

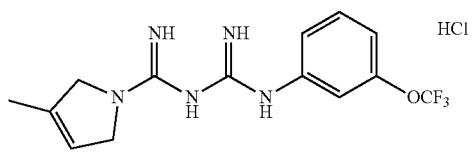 [SMILES: CC1=CCN(C(=N)NC(=N)Nc2cccc(OC(F)(F)F)c2)C1 ; Cl]

¹H NMR (600 MHz, CD₃OD) δ 7.59 (m, 1H), 7.46 (m, 2H), 7.23 (m, 1H), 5.88 (s, 1H), 4.45 (m, 2H), 4.16 (m, 2H), 1.83 (m, 3H); LC-MS m/z 328.2 [M+1]⁺; mp 263-265° C.

Example 26: N1-(3-methyl)-1,2-dihydropyrrole-N5-(4-trifluoromethyl)benzyl biguanide hydrochloride

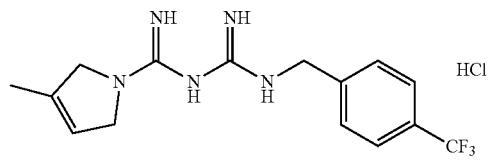 [SMILES: CC1=CCN(C(=N)NC(=N)NCc2ccc(C(F)(F)F)cc2)C1 ; Cl]

¹H NMR (600 MHz, CD₃OD) δ 7.74 (m, 1H), 7.64 (m, 2H), 7.51 (m, 1H), 5.56 (s, 1H), 4.48 (s, 2H), 4.19 (m, 4H), 1.83 (m, 3H); LC-MS m/z 326.2 [M+1]⁺; mp 267-269° C.

Example 27: N1-(3-methyl)-1,2-dihydropyrrole-N5-(4-chloro, 3-trifluoromethyl)benzyl biguanide hydrochloride

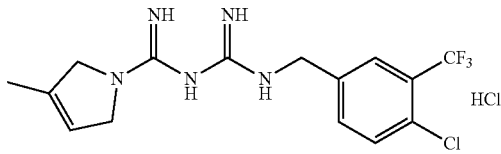 [SMILES: CC1=CCN(C(=N)NC(=N)NCc2ccc(Cl)c(C(F)(F)F)c2)C1 ; Cl]

¹H NMR (600 MHz, CD₃OD) δ 7.61 (m, 1H), 7.59 (m, 2H), 7.51 (m, 1H), 5.59 (s, 1H), 4.48 (s, 2H), 4.26 (m, 4H), 1.85 (s, 3H); LC-MS m/z 326.2 [M+1]⁺; mp 230-232° C.

Example 28: N1-1,2,3,6-tetrahydropyridine-N5-(4-trifluoromethoxy)phenyl biguanide hydrochloride

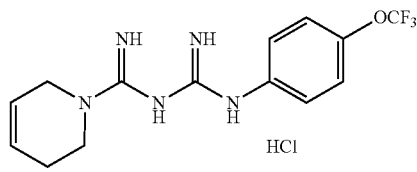 [SMILES: N=C(NC(=N)N1CC=CCC1)Nc1ccc(OC(F)(F)F)cc1 ; Cl]

¹H NMR (600 MHz, CD₃OD) δ 7.46 (d, 2H), 7.24 (d, 2H), 5.95 (m, 1H), 5.74 (m, 1H), 4.00 (s, 2H), 3.64 (t, 2H), 2.23 (s, 2H); LC-MS m/z 328.1 [M+1]⁺

Example 29: N1-1,2,3,6-tetrahydropyridine-N5-(4-trifluoromethyl)phenyl biguanide hydrochloride

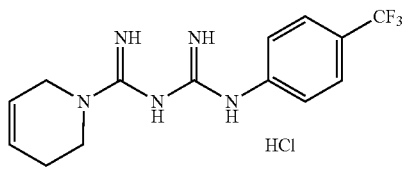 [SMILES: N=C(NC(=N)N1CC=CCC1)Nc1ccc(C(F)(F)F)cc1 ; Cl]

¹H NMR (600 MHz, CD₃OD) δ 7.59 (m, 4H), 5.96 (m, 1H), 5.75 (m, 1H), 4.01 (s, 2H), 3.65 (t, 2H), 2.25 (s, 2H); LC-MS m/z 312.2 [M+1]⁺

Example 30: N1-1,2,3,6-tetrahydropyridine-N5-(3-trifluoromethoxy)phenyl biguanide hydrochloride

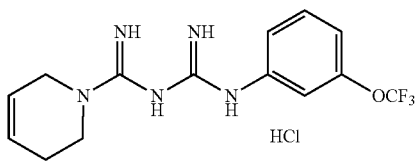 [SMILES: N=C(NC(=N)N1CC=CCC1)Nc1cccc(OC(F)(F)F)c1 ; Cl]

¹H NMR (600 MHz, CD₃OD) δ 7.82 (s, 1H), 7.57 (d, 1H), 7.49 (t, 1H), 7.38 (d, 1H), 5.97 (m, 1H), 5.74 (m, 1H), 4.01 (s, 2H), 3.65 (t, 2H), 2.24 (s, 2H)

Example 31: N1-1,2,3,6-tetrahydropyridine-N5-(3-trifluoromethyl)phenyl biguanide hydrochloride

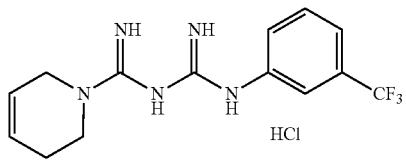 [SMILES: N=C(NC(=N)N1CC=CCC1)Nc1cccc(C(F)(F)F)c1 ; Cl]

¹H NMR (600 MHz, CD₃OD) δ 7.82 (s, 1H), 7.57 (d, 1H), 7.49 (t, 1H), 7.37 (d, 1H), 5.95 (m, 1H), 5.74 (m, 1H), 4.01 (s, 2H), 3.65 (t, 2H), 2.24 (s, 2H); LC-MS m/z 312.2 [M+1]⁺

Example 32: N1-1,2,3,6-tetrahydropyridine-N5-(4-fluoro, 3-trifluoromethyl)phenyl biguanide hydrochloride

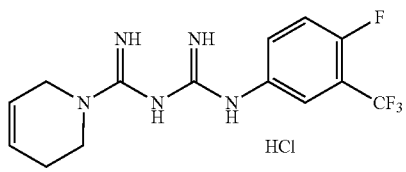 [SMILES: N=C(NC(=N)N1CC=CCC1)Nc1ccc(F)c(C(F)(F)F)c1 ; Cl]

$^1$H NMR (600 MHz, CD$_3$OD) δ 7.80 (m, 1H), 7.60 (m, 1H), 7.28 (t, 1H), 5.95 (m, 1H), 5.73 (m, 1H), 4.00 (s, 2H), 3.64 (t, 2H), 2.23 (s, 2H); LC-MS m/z 330.2 [M+1]$^+$

Example 33:
N1-1,2,3,6-tetrahydropyridine-N5-(4-chloro, 3-trifluoromethyl)phenyl biguanide hydrochloride

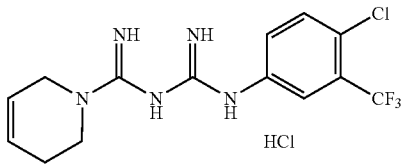

$^1$H NMR (600 MHz, CD$_3$OD) δ 7.93 (m, 1H), 7.59 (m, 1H), 7.53 (d, 1H), 5.96 (m, 1H), 5.74 (m, 1H), 4.01 (s, 2H), 3.65 (t, 2H), 2.24 (s, 2H); LC-MS m/z 346.0 [M+1]$^+$

Example 34:
N1-1,2,3,6-tetrahydropyridine-N5-(3-fluoro, 4-trifluoromethoxy)phenyl biguanide hydrochloride

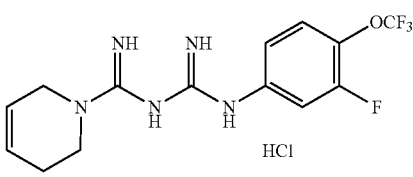 [SMILES: N=C(NC(=N)N1CC=CCC1)Nc1ccc(OC(F)(F)F)c(F)c1 ; Cl]

$^1$H NMR (600 MHz, CD$_3$OD) δ 7.56 (m, 1H), 7.34 (t, 1H), 7.16 (m, 1H), 5.97 (m, 1H), 5.74 (m, 1H), 4.01 (s, 2H), 3.65 (t, 2H), 2.25 (s, 2H); LC-MS m/z 346.2 [M+1]$^+$

Example 35:
N1-1,2,3,6-tetrahydropyridine-N5-(4-chloro)phenyl biguanide hydrochloride

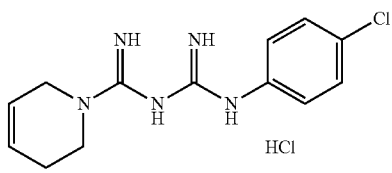

$^1$H NMR (600 MHz, CD$_3$OD) δ 7.37 (d, 2H), 7.31 (d, 2H), 5.97 (m, 1H), 5.74 (m, 1H), 3.99 (s, 2H), 3.63 (t, 2H), 2.23 (s, 2H); LC-MS m/z 278.2 [M+1]$^+$

Example 36:
N1-1,2,3,6-tetrahydropyridine-N5-(4-bromo)phenyl biguanide hydrochloride

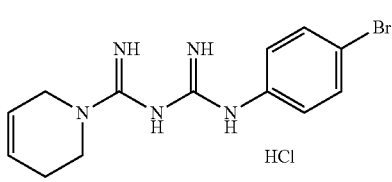 [SMILES: N=C(NC(=N)N1CC=CCC1)Nc1ccc(Br)cc1 ; Cl]

$^1$H NMR (600 MHz, CD$_3$OD) δ 7.45 (d, 2H), 7.30 (d, 2H), 5.97 (m, 1H), 5.74 (m, 1H), 3.99 (s, 2H), 3.63 (t, 2H), 2.23 (s, 2H); LC-MS m/z 323.0 [M+1]$^+$

Example 37:
N1-1,2,3,6-tetrahydropyridine-N5-(4-fluoro)phenyl biguanide hydrochloride

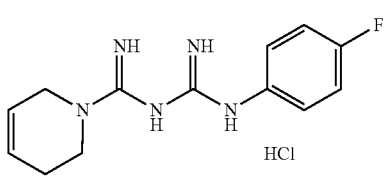 [SMILES: N=C(NC(=N)N1CC=CCC1)Nc1ccc(F)cc1 ; Cl]

$^1$H NMR (600 MHz, CD$_3$OD) δ 7.35 (d, 2H), 7.07 (d, 2H), 5.94 (m, 1H), 5.72 (m, 1H), 3.97 (s, 2H), 3.62 (t, 2H), 2.23 (s, 2H); LC-MS m/z 262.2 [M+1]$^+$

Example 38: N1-1,2,3,6-tetrahydropyridine-N5-(3, 5-dimethoxy)phenyl biguanide hydrochloride

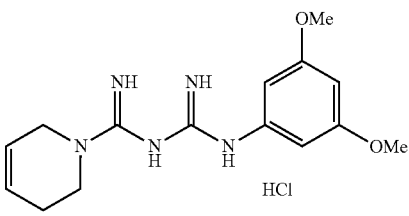 [SMILES: COc1cc(NC(=N)NC(=N)N2CC=CCC2)cc(OC)c1 ; Cl]

$^1$H NMR (600 MHz, CD$_3$OD) δ 6.56 (d, 2H), 6.27 (t, 1H), 5.96 (m, 1H), 5.74 (m, 1H), 4.00 (s, 2H), 3.76 (s, 6H), 3.64 (t, 2H), 2.23 (s, 2H); LC-MS m/z 304.2 [M+1]$^+$

Example 39:
N1-1,2,3,6-tetrahydropyridine-N5-phenyl biguanide hydrochloride

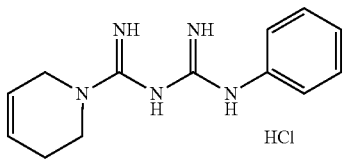 [SMILES: N=C(NC(=N)N1CC=CCC1)Nc1ccccc1 ; Cl]

$^1$H NMR (600 MHz, CD$_3$OD) δ 7.33 (m, 4H), 7.13 (m, 1H), 5.94 (m, 1H), 5.73 (m, 1H), 3.98 (s, 2H), 3.63 (t, 2H), 2.22 (s, 2H); LC-MS m/z 244.2 [M+1]$^+$

Example 40:
N1-1,2,3,6-tetrahydropyridine-N5-(4-methoxy)phenyl biguanide hydrochloride

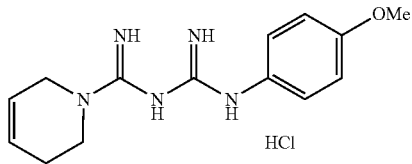 [SMILES: COc1ccc(NC(=N)NC(=N)N2CC=CCC2)cc1 ; Cl]

¹H NMR (600 MHz, CD₃OD) δ 7.23 (d, 2H), 6.91 (d, 2H) 5.93 (m, 1H), 5.72 (m, 1H), 3.96 (s, 2H), 3.78 (s, 3H), 3.61 (t, 2H), 2.21 (s, 2H); LC-MS m/z 274.2 [M+1]⁺

Example 41:
N1-1,2,3,6-tetrahydropyridine-N5-(3-methoxy)phenyl biguanide hydrochloride

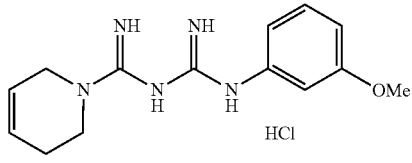 [SMILES: COc1cccc(NC(=N)NC(=N)N2CC=CCC2)c1 ; Cl]

¹H NMR (600 MHz, CD₃OD) δ 7.22 (t, 1H), 7.00 (t, 1H), 6.88 (m, 1H), 6.71 (m, 1H), 5.95 (m, 1H), 5.74 (m, 1H), 3.99 (s, 2H), 3.77 (s, 3H), 3.64 (t, 2H), 2.23 (s, 2H); LC-MS m/z 274.2 [M+1]⁺

Example 42:
N1-1,2-dihydropyrrole-N5-(4-methoxy)phenyl biguanide hydrochloride

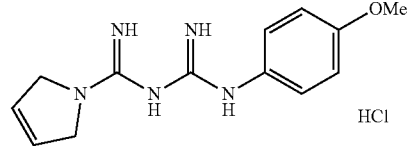 [SMILES: COc1ccc(NC(=N)NC(=N)N2CC=CC2)cc1 ; Cl]

¹H NMR (600 MHz, CD₃OD) δ 7.25 (d, 2H), 6.91 (d, 2H), 5.92 (s, 2H), 4.22 (d, 4H), 3.78 (s, 3H); LC-MS m/z 260.2 [M+1]⁺

Example 43:
N1-1,2-dihydropyrrole-N5-(3-methoxy)phenyl biguanide hydrochloride

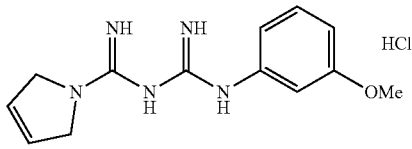 [SMILES: COc1cccc(NC(=N)NC(=N)N2CC=CC2)c1 ; Cl]

¹H NMR (600 MHz, CD₃OD) δ 7.22 (t, 1H), 7.03 (t, 1H), 6.91 (m, 1H), 6.71 (m, 1H), 5.93 (s, 2H), 4.29 (d, 4H), 3.77 (s, 3H); LC-MS m/z 260.2 [M+1]⁺

Example 44: N1-1,2-dihydropyrrole-N5-phenyl biguanide hydrochloride

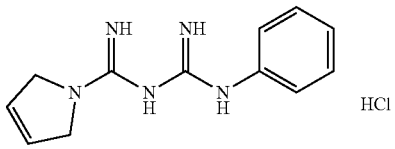 [SMILES: N=C(NC(=N)N1CC=CC1)Nc1ccccc1 ; Cl]

¹H NMR (600 MHz, CD₃OD) δ 7.37 (m, 4H), 7.12 (t, 1H), 5.93 (s, 2H), 4.27 (d, 4H); LC-MS m/z 230.2 [M+1]⁺

Example 45:
N1-1,2-dihydropyrrole-N5-(3,5-dimethoxy)phenyl biguanide hydrochloride

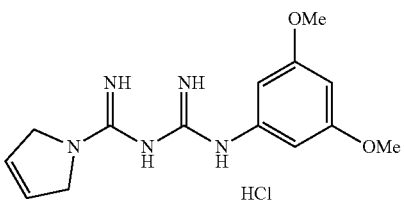 [SMILES: COc1cc(NC(=N)NC(=N)N2CC=CC2)cc(OC)c1 ; Cl]

¹H NMR (600 MHz, CD₃OD) δ 6.58 (d, 2H), 6.27 (t, 1H), 5.93 (m, 1H), 4.30 (d, 4H), 3.75 (s, 6H); LC-MS m/z 290.2 [M+1]⁺

Example 46: N1-1,2-dihydropyrrole-N5-(4-fluoro, 3-trifluoromethyl)phenyl biguanide hydrochloride

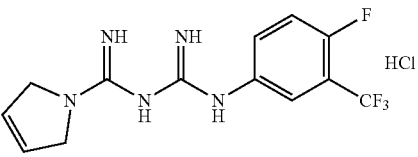 [SMILES: N=C(NC(=N)N1CC=CC1)Nc1ccc(F)c(C(F)(F)F)c1 ; Cl]

¹H NMR (600 MHz, CD₃OD) δ 7.82 (m, 1H), 7.64 (m, 1H), 7.29 (t, 1H), 5.94 (s, 2H), 4.26 (d, 4H); LC-MS m/z 316.2 [M+1]⁺

Example 47: N1-1,2-dihydropyrrole-N5-(3-fluoro, 4-trifluoromethyl)phenyl biguanide hydrochloride

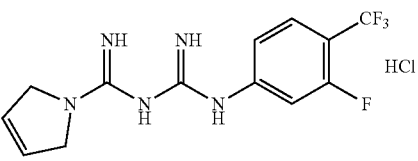 [SMILES: N=C(NC(=N)N1CC=CC1)Nc1ccc(C(F)(F)F)c(F)c1 ; Cl]

¹H NMR (600 MHz, CD₃OD) δ 7.21 (m, 2H), 7.15 (d, 2H), 5.94 (m, 1H), 5.73 (m, 1H), 3.97 (s, 2H), 3.62 (t, 2H), 2.30 (s, 3H), 2.22 (s, 2H); LC-MS m/z 316.2 [M+1]⁺

Example 48:
N1-1,2,3,6-tetrahydropyridine-N5-(4-methyl)phenyl biguanide hydrochloride

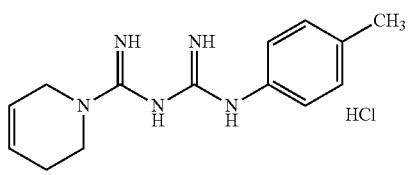 [SMILES: Cc1ccc(NC(=N)NC(=N)N2CC=CCC2)cc1 ; Cl]

¹H NMR (600 MHz, CD₃OD) δ 7.21 (m, 2H), 7.15 (d, 2H), 5.94 (m, 1H), 5.73 (m, 1H), 3.97 (s, 2H), 3.62 (t, 2H), 2.30 (s, 3H), 2.22 (s, 2H); LC-MS m/z 258.2 [M+1]⁺

Example 49:
N1-1,2,3,6-tetrahydropyridine-N5-(3-methyl)phenyl biguanide hydrochloride

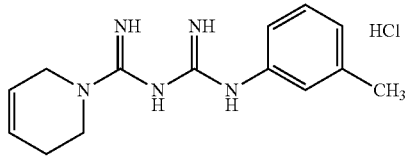 [SMILES: Cc1cccc(NC(=N)NC(=N)N2CC=CCC2)c1 ; Cl]

¹H NMR (600 MHz, CD₃OD) δ 7.21 (m, 3H), 6.96 (d, 2H), 5.95 (m, 1H), 5.73 (m, 1H), 3.98 (s, 2H), 3.63 (t, 2H), 2.32 (s, 3H), 2.22 (s, 2H); LC-MS m/z 258.2 [M+1]⁺

Example 50:
N1-1,2-dihydropyrrole-N5-(4-methyl)phenyl biguanide hydrochloride

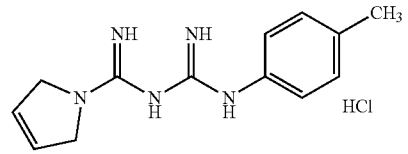 [SMILES: Cc1ccc(NC(=N)NC(=N)N2CC=CC2)cc1 ; Cl]

¹H NMR (600 MHz, CD₃OD) δ 7.24 (d, 2H), 7.15 (d, 2H), 5.92 (s, 2H), 4.26 (d, 4H), 2.31 (s, 3H); LC-MS m/z 244.2 [M+1]⁺

Example 51:
N1-1,2-dihydropyrrole-N5-(3-methyl)phenyl biguanide hydrochloride

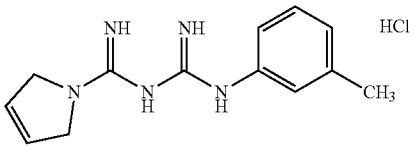 [SMILES: Cc1cccc(NC(=N)NC(=N)N2CC=CC2)c1 ; Cl]

¹H NMR (600 MHz, CD₃OD) δ 7.17 (m, 3H), 6.96 (d, 1H), 5.93 (s, 2H), 4.27 (d, 4H), 2.32 (s, 3H); LC-MS m/z 244.2 [M+1]⁺

Example 52: N1-1,2-dihydropyrrole-N5-(3-trifluoromethoxy)phenyl biguanide hydrochloride

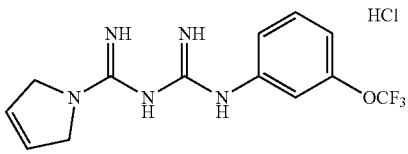 [SMILES: N=C(NC(=N)N1CC=CC1)Nc1cccc(OC(F)(F)F)c1 ; Cl]

¹H NMR (600 MHz, CD₃OD) δ 7.83 (s, 1H), 7.61 (d, 1H), 7.49 (t, 1H), 7.38 (d, 1H), 5.94 (s, 2H), 4.28 (d, 4H)

Example 53:
N1-1,2,3,6-tetrahydropyridine-N5-hexyl biguanide hydrochloride

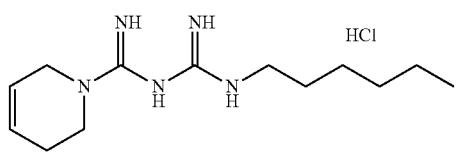 [SMILES: CCCCCCNC(=N)NC(=N)N1CC=CCC1 ; Cl]

¹H NMR (600 MHz, CD₃OD) δ 5.93 (m, 1H), 5.72 (m, 1H), 3.98 (m, 2H), 3.63 (t, 2H), 3.20 (t, 2H), 2.23 (t, 2H), 1.70-1.33 (m, 8H), 0.91 (t, 3H); LC-MS m/z 252.4 [M+1]⁺

Example 54: N1-1,2,3,6-tetrahydropyridine-N5-(4-trifluoromethoxy)benzyl biguanide hydrochloride

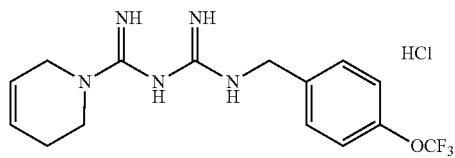 [SMILES: N=C(NCc1ccc(OC(F)(F)F)cc1)NC(=N)N1CC=CCC1 ; Cl]

¹H NMR (600 MHz, CD₃OD) δ 7.43 (d, 2H), 7.25 (d, 2H), 5.91 (m, 1H), 5.68 (m, 1H), 4.43 (s, 2H), 3.90 (m, 2H), 3.52 (t, 2H), 2.16 (s, 2H); LC-MS m/z 342.2 [M+1]⁺

Example 55: N1-1,2,3,6-tetrahydropyridine-N5-(3-trifluoromethoxy)benzyl biguanide hydrochloride

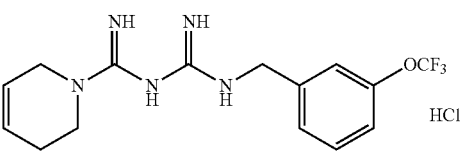 [SMILES: N=C(NCc1cccc(OC(F)(F)F)c1)NC(=N)N1CC=CCC1 ; Cl]

¹H NMR (600 MHz, CD₃OD) δ 7.43 (t, 1H), 7.33 (d, 1H), 7.25 (s, 1H), 7.18 (d, 1H), 5.91 (m, 1H), 5.68 (m, 1H), 4.45 (s, 2H), 3.90 (t, 2H), 3.52 (t, 2H), 2.15 (s, 2H); LC-MS m/z 342.2 [M+1]⁺

Example 56: N1-1,2,3,6-tetrahydropyridine-N5-(4-trifluoromethyl)benzyl biguanide hydrochloride

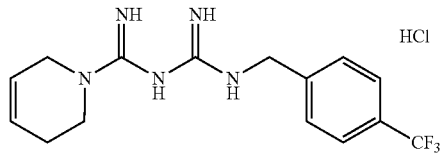 [SMILES: N=C(NCc1ccc(C(F)(F)F)cc1)NC(=N)N1CC=CCC1 ; Cl]

¹H NMR (600 MHz, CD₃OD) δ 7.64 (d, 2H), 7.52 (d, 2H), 5.91 (m, 1H), 5.67 (m, 1H), 4.49 (s, 2H), 3.89 (t, 2H), 3.51 (t, 2H), 2.14 (s, 2H); LC-MS m/z 326.2 [M+1]⁺

Example 57: N1-1,2,3,6-tetrahydropyridine-N5-(3-trifluoromethyl)benzyl biguanide hydrochloride

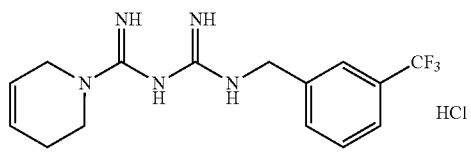 [SMILES: N=C(NCc1cccc(C(F)(F)F)c1)NC(=N)N1CC=CCC1 ; Cl]

¹H NMR (600 MHz, CD₃OD) δ 7.64 (s, 1H), 7.56 (m, 3H), 5.91 (m, 1H), 5.67 (m, 1H), 4.48 (s, 2H), 3.89 (t, 2H), 3.51 (t, 2H), 2.15 (s, 2H); LC-MS m/z 326.2 [M+1]⁺

Example 58: N1-1,2,3,6-tetrahydropyridine-N5-(4-chloro, 3-trifluoromethyl)benzyl biguanide hydrochloride

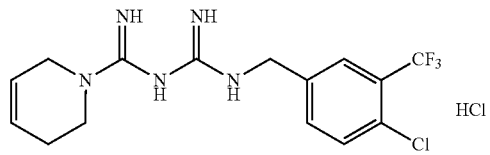 [SMILES: N=C(NCc1ccc(Cl)c(C(F)(F)F)c1)NC(=N)N1CC=CCC1 ; Cl]

¹H NMR (600 MHz, CD₃OD) δ 7.74 (s, 1H), 7.56 (m, 2H), 5.91 (m, 1H), 5.68 (m, 1H), 4.45 (s, 2H), 3.89 (t, 2H), 3.51 (t, 2H), 2.15 (s, 2H); LC-MS m/z 360.2 [M+1]⁺

Example 59: N1-1,2,3,6-tetrahydropyridine-N5-butyl biguanide hydrochloride

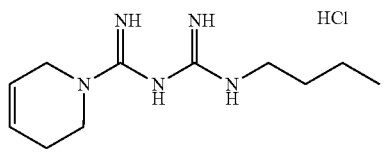 [SMILES: Cl ; CCCCNC(=N)NC(=N)N1CC=CCC1]

¹H NMR (600 MHz, CD₃OD) δ 5.94 (m, 1H), 5.73 (m, 1H), 4.19 (t, 1H), 3.98 (m, 2H), 3.64 (t, 2H), 3.20 (t, 1H), 2.23 (t, 2H), 1.70-1.37 (m, 4H), 0.95 (m, 3H); LC-MS m/z 224.2 [M+1]⁺

Example 60: N1-1,2,3,6-tetrahydropyridine-N5-propyl biguanide hydrochloride

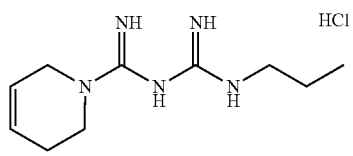

¹H NMR (600 MHz, CD₃OD) δ 5.94 (m, 1H), 5.73 (m, 1H), 3.97 (m, 2H), 3.62 (t, 2H), 3.16 (t, 2H), 2.23 (t, 2H), 1.58 (m, 2H), 0.95 (m, 3H); LC-MS m/z 210.2 [M+1]⁺

Example 61: N1-1,2,3,6-tetrahydropyridine biguanide hydrochloride

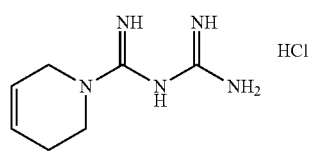 [SMILES: N=C(N)NC(=N)N1CC=CCC1 ; Cl]

¹H NMR (600 MHz, CD₃OD) δ 5.97 (m, 1H), 5.77 (m, 1H), 3.98 (m, 2H), 3.64 (m, 2H), 2.40 (m, 1H), 2.23 (m, 1H); LC-MS m/z 168.2 [M+1]⁺

Example 62: Synthesis of N1-(3-methyl)piperidine cyanoguanidine

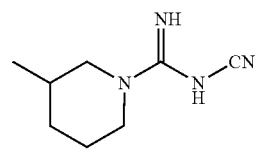

Concentrated hydrochloric acid (0.9 mL, 0.010 mol) was added to a butanol (10 mL) solution containing 3-methyl-piperidine (1.00 g, 0.010 mol), and stirred at 0° C. for 30 minutes. Sodium dicyanamide (0.99 g, 0.011 mol) was added to the mixed solution, and the resulting reaction mixture was stirred for 24 hours under reflux.

After completion of the reaction was confirmed, sodium chloride formed by filtering the reaction mixture was removed, and the filtrate was then concentrated at a reduced pressure. Ethyl acetate (10 mL) was then added to the concentrate, and stirred at room temperature for an hour. The formed solid was filtered, and the filtrate was washed with ethyl acetate (2×20 mL). The filtrate was dried at a reduced pressure to obtain a white solid target compound (1.34 g, 80.0%).

¹H NMR (600 MHz, CD₃OD) δ 3.97 (m, 2H), 2.85 (m, 1H), 2.52 (m, 1H), 1.84-1.45 (m, 4H), 1.17 (m, 1H), 0.92 (d, 3H)

Example 63: Synthesis of N1-(2-methyl)piperidine cyanoguanidine

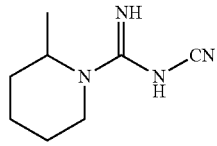

A white solid target compound (1.0 g, 37%) was prepared in the same manner as in Example 62, except that N1-(2-methyl)piperidine was used instead of the N1-(3-methyl) piperidine used in Example 62.

$^1$H NMR (600 MHz, CD$_3$OD) δ 3.98 (m, 2H), 2.85 (m, 1H), 2.53 (m, 1H), 1.82 (m, 1H), 1.71 (m, 1H), 1.59 (m, 1H), 1.48 (m, 1H), 1.91 (s, 3H); LC-MS m/z 167.2 [M+1]$^+$

Example 64: Synthesis of N1-(2,6-dimethyl)piperidine cyanoguanidine

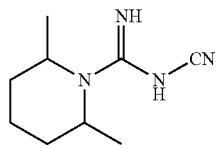

A white solid target compound (0.75 g, 47.2%) was prepared in the same manner as in Example 62, except that N1-(2,6-dimethyl)piperidine was used instead of the N1-(3-methyl)piperidine used in Example 62.

$^1$H NMR (600 MHz, CD$_3$OD) δ 4.31 (s, 2H), 1.85 (m, 1H), 1.70 (m, 4H), 1.50 (m, 1H), 1.48 (d, 6H); LC-MS m/z 181.2 [M+1]$^+$

Example 65: N1-(3-methyl)piperidine-N5-(3-trifluoromethyl)benzyl biguanide hydrochloride

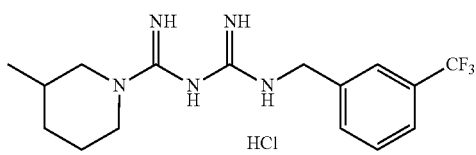 [SMILES: CC1CCCN(C(=N)NC(=N)NCc2cccc(C(F)(F)F)c2)C1 ; Cl]

Concentrated hydrochloric acid (0.24 mL, 2.71 mmol) was added to a butanol (10 mL) solution containing (3-trifluoromethyl)benzylamine (0.28 mL, 1.99 mmol) at room temperature, and then stirred for 30 minutes. The N1-(3-methyl)piperidine cyanoguanidine (300 mg, 1.81 mmol) obtained in Example 1 was added to the reaction mixture, and then stirred for 2 hours under reflux. The reaction mixture was concentrated at a reduced pressure, and ethyl acetate (3 mL) was added to the concentrated reaction mixture. The formed solid was filtered, and the filtrate was then dried at a reduced pressure to obtain a white solid target compound (0.37 g, 54.7%).

$^1$H NMR (600 MHz, CD$_3$OD) δ 7.63 (m, 1H), 7.55 (m, 3H), 4.47 (s, 2H), 3.85 (dd, 2H), 2.86 (t, 1H), 2.54 (m, 1H), 1.80 (m, 1H), 1.67 (m, 1H), 1.56 (m, 1H), 1.47 (m, 1H), 1.17 (q, 1H), 0.85 (d, 3H); LC-MS m/z 342.2 [M+1]$^+$

Target compounds of the following Examples 66 to 98 were prepared in the same manner as in Example 65, except that the cyanoguanidine and amine compounds synthesized in Examples 63 and 64, which corresponded to the target compounds, were used respectively instead of the N1-(3-methyl)piperidine cyanoguanidine synthesized in Example 62 and the (3-trifluoromethyl)benzylamine used in Example 65.

Example 66: N1-(3-methyl)piperidine-N5-(4-chloro)benzyl biguanide hydrochloride

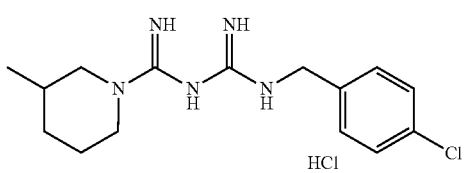 [SMILES: CC1CCCN(C(=N)NC(=N)NCc2ccc(Cl)cc2)C1 ; Cl]

$^1$H NMR (600 MHz, CD$_3$OD) δ 7.28 (m, 4H), 4.29 (m, 2H), 3.82 (m, 2H), 2.81 (m, 1H), 2.51 (m, 1H), 1.57 (m, 4H), 1.15 (m, 1H) 0.84 (m, 3H); LC-MS m/z 308.2 [M+1]$^+$; mp 256-258° C.

Example 67: N1-(3-methyl)piperidine-N5-(4-fluoro)phenyl biguanide hydrochloride

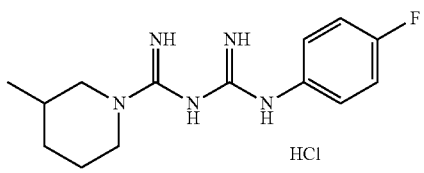 [SMILES: CC1CCCN(C(=N)NC(=N)Nc2ccc(F)cc2)C1 ; Cl]

$^1$H NMR (600 MHz, CD$_3$OD) δ 7.40 (m, 4H), 4.29 (m, 2H), 3.89 (m, 2H), 2.94 (m, 1H), 2.67 (m, 1H), 1.70 (m, 4H), 1.18 (m, 1H) 0.87 (m, 3H); LC-MS m/z 278.2 [M+1]$^+$; mp 265-267° C.

Example 68: N1-(3-methyl)piperidine-N5-(4-bromo)phenyl biguanide hydrochloride

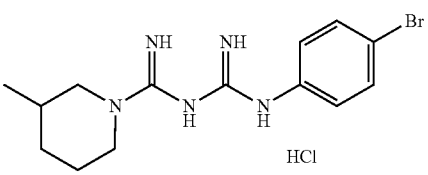 [SMILES: CC1CCCN(C(=N)NC(=N)Nc2ccc(Br)cc2)C1 ; Cl]

$^1$H NMR (600 MHz, CD$_3$OD) δ 7.36 (m, 2H), 7.06 (m, 2H), 3.89 (m, 2H), 2.89 (m, 1H), 2.61 (m, 1H), 1.66 (m, 4H), 1.17 (m, 1H), 0.86 (m, 3H); LC-MS m/z 339.2 [M+1]$^+$; mp 252-254° C.

Example 69: N1-(3-methyl)piperidine-N5-(4-chloro, 3-trifluoromethyl)phenyl biguanide hydrochloride

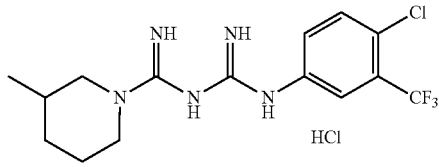

$^1$H NMR (600 MHz, CD$_3$OD) δ 7.93 (m, 1H), 7.51 (m, 2H), 3.92 (m, 2H), 2.99 (m, 1H), 2.69 (m, 1H), 1.86 (m, 1H), 1.73 (m, 2H), 1.56 (m, 1H), 1.20 (m, 1H), 0.91 (m, 3H); LC-MS m/z 362.2 [M+1]$^+$; mp 230-232° C.

Example 70: N1-(3-methyl)piperidine-N5-(3-fluoro, 4-trifluoromethyl)phenyl biguanide hydrochloride

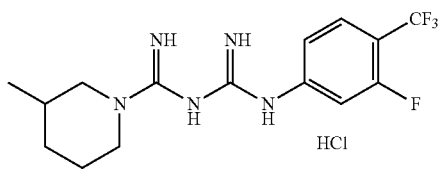 [SMILES: CC1CCCN(C(=N)NC(=N)Nc2ccc(C(F)(F)F)c(F)c2)C1 ; Cl]

$^1$H NMR (600 MHz, CD$_3$OD) δ 7.57 (m, 2H), 7.21 (m, 1H), 3.92 (m, 2H), 3.00 (m, 1H), 2.72 (m, 1H), 1.88 (m, 1H), 1.71 (m, 3H), 1.24 (m, 1H), 0.91 (m, 3H); LC-MS m/z 346.2 [M+1]$^+$; mp 228-230° C.

Example 71: N1-(3-methyl)piperidine-N5-(4-fluoro, 3-trifluoromethyl)phenyl biguanide hydrochloride

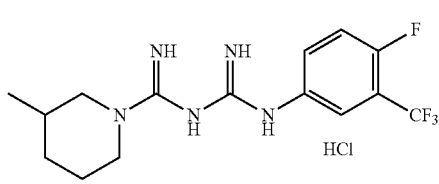 [SMILES: CC1CCCN(C(=N)NC(=N)Nc2ccc(F)c(C(F)(F)F)c2)C1 ; Cl]

$^1$H NMR (600 MHz, CD$_3$OD) δ 7.85 (m, 2H), 7.60 (m, 1H), 7.29 (t, J=9.6 Hz, 1H), 3.93 (m, 2H), 3.02 (m, 1H), 2.70 (m, 1H), 1.88 (m, 1H), 1.77 (m, 2H), 1.58 (m, 1H), 1.25 (m, 1H), 0.95 (m, 3H); LC-MS m/z 346.2 [M+1]$^+$; mp 243-245° C.

Example 72: N1-(2-methyl)piperidine-N5-(4-trifluoromethoxy)phenyl biguanide hydrochloride

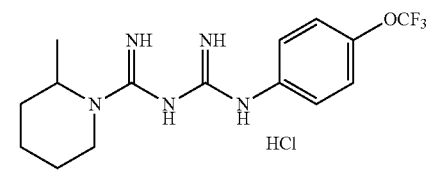 [SMILES: CC1CCCCN1C(=N)NC(=N)Nc1ccc(OC(F)(F)F)cc1 ; Cl]

$^1$H NMR (600 MHz, CD$_3$OD) δ 7.42 (m, 2H), 7.20 (m, 2H), 4.35 (m, 1H), 3.88 (m, 1H), 3.06 (m, 1H), 1.71 (m, 3H), 1.59 (m, 2H), 1.48 (m, 1H), 1.22 (s, 3H); LC-MS m/z 344.2 [M+1]$^+$; mp 250-252° C.

Example 73: N1-(2-methyl)piperidine-N5-(3-trifluoromethoxy)phenyl biguanide hydrochloride

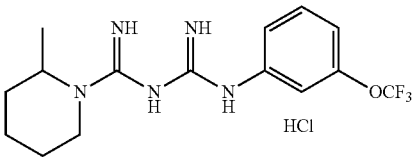 [SMILES: CC1CCCCN1C(=N)NC(=N)Nc1cccc(OC(F)(F)F)c1 ; Cl]

$^1$H NMR (600 MHz, CD$_3$OD) δ 7.52 (m, 1H), 7.37 (m, 1H), 7.25 (m, 1H), 6.96 (m, 1H), 4.41 (m, 1H), 3.91 (m, 1H), 3.13 (m, 1H), 1.74 (m, 3H), 1.64 (m, 2H), 1.51 (m, 1H) 1.26 (m, 3H); LC-MS m/z 344.2 [M+1]$^+$; mp 246-248° C.

Example 74: N1-(2-methyl)piperidine-N5-(4-trifluoromethyl)phenyl biguanide hydrochloride

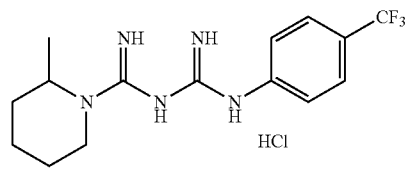 [SMILES: CC1CCCCN1C(=N)NC(=N)Nc1ccc(C(F)(F)F)cc1 ; Cl]

$^1$H NMR (600 MHz, CD$_3$OD) δ 7.56 (m, 4H), 4.37 (m, 1H), 3.91 (m, 1H), 3.12 (m, 1H), 1.73 (m, 3H), 1.61 (m, 2H), 1.52 (m, 1H) 1.24 (m, 3H); LC-MS m/z 329.2 [M+1]$^+$; mp 252-254° C.

Example 75: N1-(3-methyl)piperidine-N5-(3-fluoro, 4-trifluoromethoxy)phenyl biguanide hydrochloride

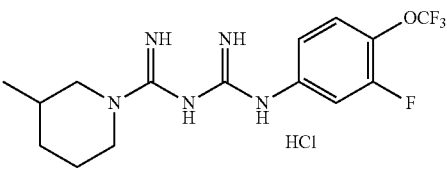 [SMILES: CC1CCCN(C(=N)NC(=N)Nc2ccc(OC(F)(F)F)c(F)c2)C1 ; Cl]

$^1$H NMR (600 MHz, CD$_3$OD) δ 7.50 (m, 1H), 7.23 (m, 1H), 7.08 (m, 1H), 2.85 (m, 2H), 2.63 (m, 1H), 1.79 (m, 1H), 1.67 (m, 3H), 1.58 (m, 1H), 1.17 (m, 1H), 0.86 (m, 3H); LC-MS m/z 362.2 [M+1]$^+$; mp 243-245° C.

Example 76: N1-(2-methyl)piperidine-N5-(3-fluoro, 4-trifluoromethoxy)phenyl biguanide hydrochloride

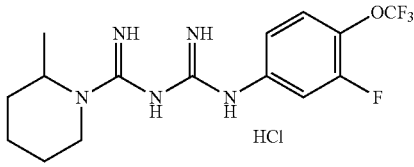 [SMILES: CC1CCCCN1C(=N)NC(=N)Nc1ccc(OC(F)(F)F)c(F)c1 ; Cl]

$^1$H NMR (600 MHz, CD$_3$OD) δ 7.58 (m, 1H), 7.36 (m, 1H), 7.16 (m, 1H), 4.41 (m, 1H), 3.92 (m, 1H), 3.16 (m, 1H), 1.70 (m, 6H) 1.29 (m, 3H); LC-MS m/z 362.0 [M+1]$^+$; mp 241-243° C.

Example 77: N1-(2-methyl)piperidine-N5-(4-chloro)phenyl biguanide hydrochloride

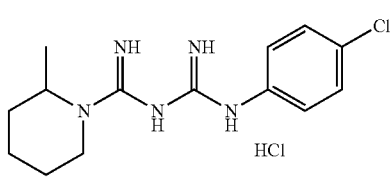 [SMILES: CC1CCCCN1C(=N)NC(=N)Nc1ccc(Cl)cc1 ; Cl]

$^1$H NMR (600 MHz, CD$_3$OD) δ 7.30 (m, 4H), 4.36 (m, 1H), 3.89 (m, 1H), 3.10 (m, 1H), 1.61 (m, 5H), 1.49 (m, 1H), 1.25 (m, 3H); LC-MS m/z 294.0 [M+1]$^+$; mp 251-253° C.

Example 78: N1-(2-methyl)piperidine-N5-(4-fluoro, 3-trifluoromethyl)phenyl biguanide hydrochloride

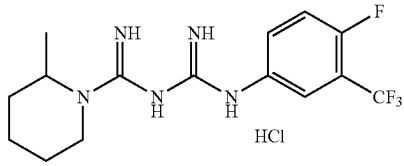 [SMILES: CC1CCCCN1C(=N)NC(=N)Nc1ccc(F)c(C(F)(F)F)c1 ; Cl]

$^1$H NMR (600 MHz, CD$_3$OD) δ 7.84 (m, 1H), 7.56 (m, 1H), 7.28 (m, 1H), 4.39 (m, 1H), 3.90 (m, 1H), 3.13 (m, 1H), 1.73 (m, 5H), 1.51 (m, 1H), 1.25 (m, 3H); LC-MS m/z 346.0 [M+1]$^+$; mp 251-253° C.

Example 79: N1-(2-methyl)piperidine-N5-(3-trifluoromethyl)phenyl biguanide hydrochloride

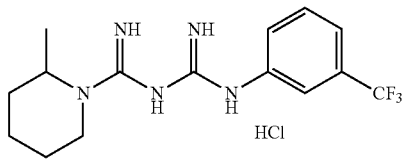 [SMILES: CC1CCCCN1C(=N)NC(=N)Nc1cccc(C(F)(F)F)c1 ; Cl]

$^1$H NMR (600 MHz, CD$_3$OD) δ 7.83 (m, 1H), 7.48 (m, 2H), 7.32 (m, 1H), 4.39 (m, 1H), 3.92 (m, 1H), 3.13 (m, 1H), 1.73 (m, 6H), 1.20 (m, 3H); LC-MS m/z 328.2 [M+1]$^+$; mp 249-251° C.

Example 80: N1-(2-methyl)piperidine-N5-(4-chloro, 3-trifluoromethyl)phenyl biguanide hydrochloride

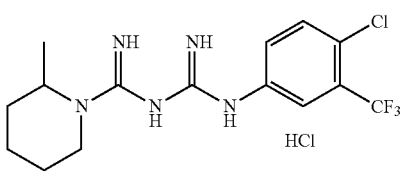 [SMILES: CC1CCCCN1C(=N)NC(=N)Nc1ccc(Cl)c(C(F)(F)F)c1 ; Cl]

$^1$H NMR (600 MHz, CD$_3$OD) δ 7.83 (m, 1H), 7.95 (m, 1H), 7.51 (m, 2H), 4.38 (m, 1H), 3.91 (m, 1H), 3.12 (m, 1H), 1.60 (m, 6H), 1.20 (m, 3H); LC-MS m/z 362.3 [M+1]$^+$; mp 316-318° C.

Example 81: N1-(3-methyl)piperidine-N5-(4-trifluoromethyl)phenyl biguanide hydrochloride

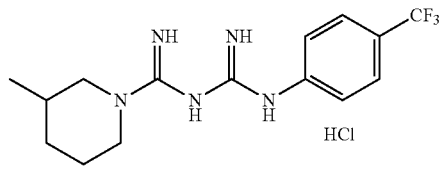 [SMILES: CC1CCCN(C(=N)NC(=N)Nc2ccc(C(F)(F)F)cc2)C1 ; Cl]

$^1$H NMR (600 MHz, CD$_3$OD) δ 7.61 (s, 4H), 3.98 (d, 2H), 3.04 (t, 1H), 2.74 (t, 1H), 1.91 (m, 1H), 1.81-1.73 (m, 2H), 1.63 (m, 1H), 1.27 (q, 1H), 0.98 (d, 3H); LC-MS m/z 328.2 [M+1]$^+$

Example 82: N1-(3-methyl)piperidine-N5-(4-trifluoromethoxy)phenyl biguanide hydrochloride

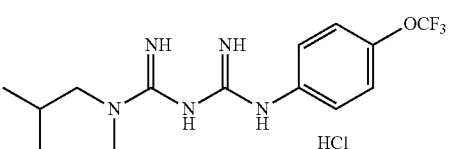

$^1$H NMR (600 MHz, CD$_3$OD) δ 7.46 (m, 2H), 7.22 (m, 2H), 3.94 (d, 2H), 2.97 (t, 1H), 2.67 (t, 1H), 1.86 (m, 1H), 1.76-1.66 (m, 2H), 1.55 (m, 1H), 1.23 (q, 1H), 0.93 (d, 3H); LC-MS m/z 344.2 [M+1]$^+$

Example 83: N1-(3-methyl)piperidine-N5-(3-trifluoromethoxy)phenyl biguanide hydrochloride

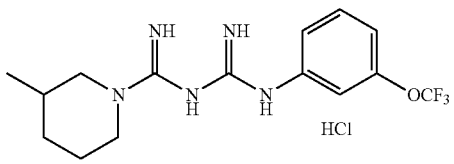 [SMILES: CC1CCCN(C(=N)NC(=N)Nc2cccc(OC(F)(F)F)c2)C1 ; Cl]

¹H NMR (600 MHz, CD₃OD) δ 7.54 (s, 1H), 7.38 (t, 1H), 7.26 (d, 1H), 6.98 (d, 1H), 3.97 (s, 2H), 3.00 (s, 1H), 2.70 (t, 1H), 1.88 (m, 1H), 1.78-1.71 (m, 2H), 1.59 (m, 1H), 1.24 (q, 1H), 0.91 (d, 3H); LC-MS m/z 344.2 [M+1]⁺

Example 84: N1-(3-methyl)piperidine-N5-(4-trifluoromethoxy)benzyl biguanide hydrochloride

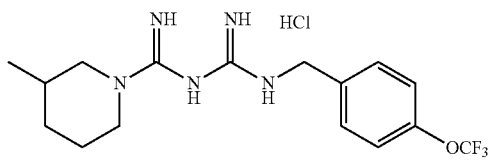 [SMILES: CC1CCCN(C(=N)NC(=N)NCc2ccc(OC(F)(F)F)cc2)C1 ; Cl]

¹H NMR (600 MHz, CD₃OD) δ 7.42 (d, 2H), 7.25 (d, 2H), 4.41 (s, 2H), 3.84 (dd, 2H), 2.85 (t, 1H), 2.52 (t, 1H), 1.82 (m, 1H), 1.66-1.55 (m, 2H), 1.47 (m, 1H), 1.16 (q, 1H), 0.84 (d, 3H); LC-MS m/z 358.2 [M+1]⁺

Example 85: N1-(3-methyl)piperidine-N5-(4-fluoro, 3-trifluoromethyl)phenyl biguanide hydrochloride

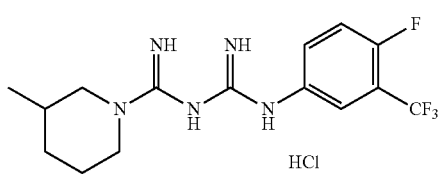 [SMILES: CC1CCCN(C(=N)NC(=N)Nc2ccc(F)c(C(F)(F)F)c2)C1 ; Cl]

¹H NMR (600 MHz, CD₃OD) δ 7.84 (dd, 1H), 7.58 (dt, 1H), 7.29 (t, 1H), 3.95 (s, 2H), 2.99 (s, 1H), 2.96 (t, 1H), 1.88 (m, 1H), 1.77 (m, 1H), 1.69 (m, 1H), 1.57 (m, 1H), 1.24 (q, 1H), 0.94 (d, 3H); LC-MS m/z 346.2 [M+1]⁺

Example 86: N1-(3-methyl)piperidine-N5-(4-trifluoromethyl)benzyl biguanide hydrochloride

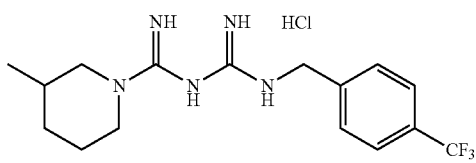 [SMILES: CC1CCCN(C(=N)NC(=N)NCc2ccc(C(F)(F)F)cc2)C1 ; Cl]

¹H NMR (600 MHz, CD₃OD) δ 7.64 (d, 2H), 7.51 (d, 2H), 4.47 (s, 2H), 3.84 (dd, 2H), 2.85 (t, 1H), 2.52 (t, 1H), 1.82 (m, 1H), 1.66 (m, 1H), 1.55 (m, 1H), 1.47 (m, 1H), 1.17 (q, 1H), 0.84 (d, 3H); LC-MS m/z 342.2 [M+1]⁺

Example 87: N1-(3-methyl)piperidine-N5-(4-chloro)phenyl biguanide hydrochloride

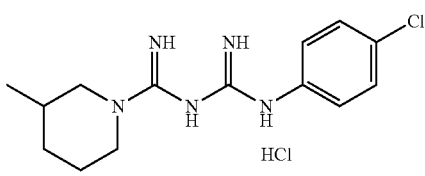 [SMILES: CC1CCCN(C(=N)NC(=N)Nc2ccc(Cl)cc2)C1 ; Cl]

¹H NMR (600 MHz, CD₃OD) δ 7.35 (m, 4H), 3.96 (m, 2H), 3.00 (m, 1H), 2.67 (m, 1H), 1.89 (m, 1H), 1.68 (m, 3H) 1.24 (m, 1H), 0.94 (m, 3H); LC-MS m/z 294.2 [M+1]⁺; mp 252-254° C.

Example 88: N1-(3-methyl)piperidine-N5-(3-trifluoromethyl)phenyl biguanide hydrochloride

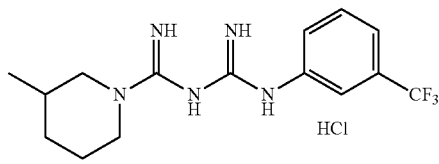 [SMILES: CC1CCCN(C(=N)NC(=N)Nc2cccc(C(F)(F)F)c2)C1 ; Cl]

¹H NMR (600 MHz, CD₃OD) δ 7.86 (m, 1H), 7.55 (d, 1H), 7.48 t, 1H), 7.37 (d, 1H), 3.97 (s, 2H), 3.01 (t, 1H), 2.71 (t, 1H), 1.89 (m, 1H), 1.77 (m, 1H), 1.70 (m, 1H), 1.59 (m, 1H), 1.25 (q, 1H), 0.94 (d, 3H); LC-MS m/z 328.2 [M+1]⁺

Example 89: N1-(2,6-dimethyl)piperidine-N5-(4-trifluoromethoxy)phenyl biguanide hydrochloride

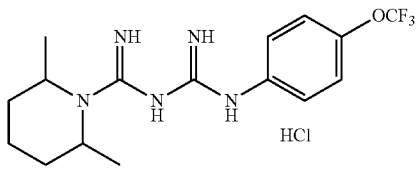 [SMILES: CC1CCCC(C)N1C(=N)NC(=N)Nc1ccc(OC(F)(F)F)cc1 ; Cl]

¹H NMR (600 MHz, CD₃OD) δ 7.46 (d, 2H), 7.23 (d, 2H), 4.60-4.10 (br s, 2H), 1.90-1.51 (m, 6H), 1.30 (s, 6H); LC-MS m/z 358.4 [M+1]⁺

Example 90: N1-(2,6-dimethyl)piperidine-N5-(3-trifluoromethoxy)phenyl biguanide hydrochloride

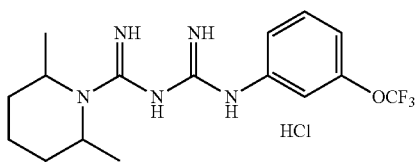 [SMILES: CC1CCCC(C)N1C(=N)NC(=N)Nc1cccc(OC(F)(F)F)c1 ; Cl]

¹H NMR (600 MHz, CD₃OD) δ 7.54 (s, 1H), 7.37 (t, 1H), 7.25 (d, 1H), 6.97 (d, 1H), 4.60-4.10 (br s, 2H), 1.91-1.52 (m, 6H), 1.31 (s, 6H); LC-MS m/z 358.4 [M+1]⁺

Example 91: N1-(2,6-dimethyl)piperidine-N5-(4-trifluoromethyl)phenyl biguanide hydrochloride

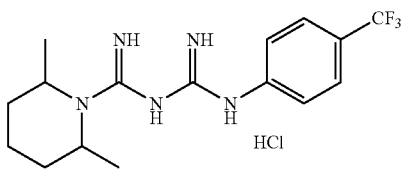 [SMILES: CC1CCCC(C)N1C(=N)NC(=N)Nc1ccc(C(F)(F)F)cc1 ; Cl]

¹H NMR (600 MHz, CD₃OD) δ 7.58 (s, 4H), 4.60-4.10 (br s, 2H), 1.93-1.52 (m, 6H), 1.32 (s, 6H); LC-MS m/z 342.4 [M+1]⁺

Example 92: N1-(2,6-dimethyl)piperidine-N5-(3-trifluoromethyl)phenyl biguanide hydrochloride

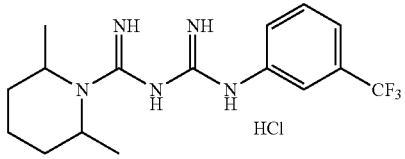 [SMILES: CC1CCCC(C)N1C(=N)NC(=N)Nc1cccc(C(F)(F)F)c1 ; Cl]

¹H NMR (600 MHz, CD₃OD) δ 7.87 (s, 1H), 7.54 (d, 1H), 7.48 (t, 1H), 7.36 (d, 1H), 4.60-4.10 (br s, 2H), 1.93-1.52 (m, 6H), 1.37 (s, 6H); LC-MS m/z 342.4 [M+1]⁺

Example 93: N1-(2,6-dimethyl)piperidine-N5-(4-fluoro, 3-trifluoromethyl)phenyl biguanide hydrochloride

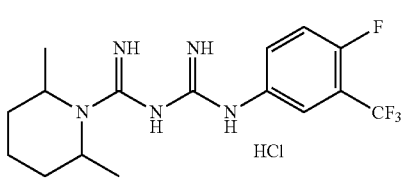 [SMILES: CC1CCCC(C)N1C(=N)NC(=N)Nc1ccc(F)c(C(F)(F)F)c1 ; Cl]

¹H NMR (600 MHz, CD₃OD) δ 7.83 (d, 1H), 7.57 (m, 1H), 7.28 (t, 1H), 4.60-4.10 (br s, 2H), 1.93-1.51 (m, 6H), 1.30 (s, 6H); LC-MS m/z 360.4 [M+1]⁺

Example 94: N1-(2,6-dimethyl)piperidine-N5-(4-chloro, 3-trifluoromethyl)phenyl biguanide hydrochloride

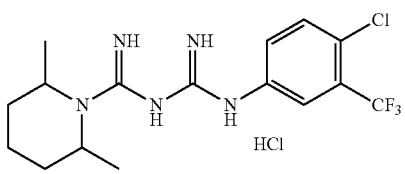

¹H NMR (600 MHz, CD₃OD) δ 7.96 (s, 1H), 7.54 (m, 2H), 4.60-4.10 (br s, 2H), 1.93-1.52 (m, 6H), 1.31 (s, 6H); LC-MS m/z 376.4 [M+1]⁺

Example 95: N1-(2,6-dimethyl)piperidine-N5-(3-fluoro, 4-trifluoromethoxy)phenyl biguanide

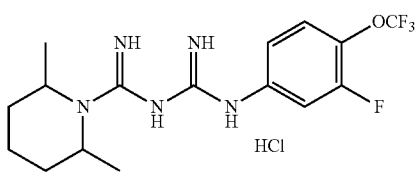 [SMILES: CC1CCCC(C)N1C(=N)NC(=N)Nc1ccc(OC(F)(F)F)c(F)c1 ; Cl]

¹H NMR (600 MHz, CD₃OD) δ 7.56 (d, 1H), 7.33 (t, 1H), 7.15 (d, 1H), 4.60-4.10 (br s, 2H), 1.93-1.52 (m, 6H), 1.32 (s, 6H); LC-MS m/z 376.4 [M+1]⁺

Example 96: N1-(2,6-dimethyl)piperidine-N5-(4-chloro)phenyl biguanide hydrochloride

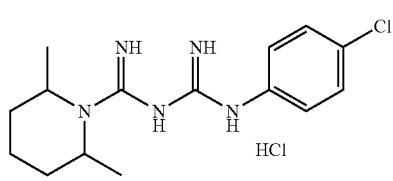 [SMILES: CC1CCCC(C)N1C(=N)NC(=N)Nc1ccc(Cl)cc1 ; Cl]

¹H NMR (600 MHz, CD₃OD) δ 7.36 (m, 2H), 7.30 (m, 2H), 4.60-4.10 (br s, 2H), 1.92-1.51 (m, 6H), 1.30 (s, 6H); LC-MS m/z 308.2, 310.2 [M+1]⁺

Example 97: N1-(2,6-dimethyl)piperidine-N5-(4-bromo)phenyl biguanide hydrochloride

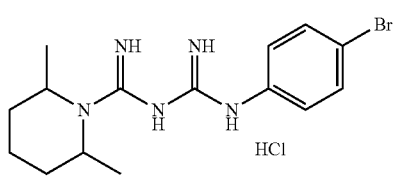 [SMILES: CC1CCCC(C)N1C(=N)NC(=N)Nc1ccc(Br)cc1 ; Cl]

¹H NMR (600 MHz, CD₃OD) δ 7.45 (d, 2H), 7.31 (d, 2H), 4.60-4.10 (br s, 2H), 1.93-1.51 (m, 6H), 1.30 (s, 6H); LC-MS m/z 353.2 [M+1]⁺

Example 98: N1-(2,6-dimethyl)piperidine-N5-(4-fluoro)phenyl biguanide hydrochloride

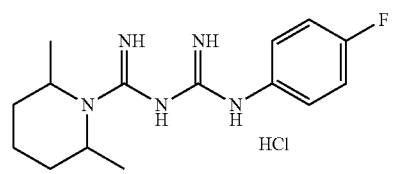 [SMILES: CC1CCCC(C)N1C(=N)NC(=N)Nc1ccc(F)cc1 ; Cl]

$^1$H NMR (600 MHz, CD$_3$OD) δ 7.37 (m, 2H), 7.05 (m, 2H), 4.60-4.10 (br s, 2H), 1.88-1.50 (m, 6H), 1.29 (s, 6H); LC-MS m/z 292.1 [M+1]$^+$

Experimental Examples

The compounds synthesized by the methods described in the examples of the present invention were evaluated for effects of AMPK activation and inhibition of cancer cell proliferation according to methods described in the following Experimental Examples.

Experimental Example 1: Measurement of AMPK Activation Effect

MCF7 cells derived from human breast cancer cells (purchased from the Korean Cell Line Bank (KCLB)) were used, and AMPK activation effects of the biguanide derivatives were confirmed using an AMPK [pT172] ELISA kit (Invitrogen, Catalog No. KHO0651).

MCF7 cells were cultured in a DMEM medium supplemented with 10% fatal bovine serum (commercially available from Gibco Life Technologies (US)). Thereafter, the cultured MCF7 cells were put into a 6-well plate with approximately 5×10$^5$ cells per well, and cultured in an incubator supplied with 5% CO$_2$. Culture media were treated with the derivatives synthesized in the Examples at concentrations of 5, 10 and 50 uM, and then cultured for 24 hours. Metformin was used as the control, and the culture media were treated with 0.05, 0.5, 1, 2, 5 and 10 mM metformin and then tested in the same manner as described for the derivatives synthesized in the Examples. Subsequently, the cells were lysed according to a method presented in the operation manual of the AMPK [pT172] ELISA kit, and 20 μg of a cell lysate was then yielded through protein assay. Thereafter, the AMPK activation effect was obtained by determining a degree of phosphorylation of a 172$^{nd}$ threonine residue (Thr172) of the AMPKα from the cell lysate according to the method presented in the operation manual of the AMPK [pT172] ELISA kit. A degree of AMPK activation by the biguanide derivatives was exhibited as a degree of AMPKα phosphorylation in cells cultured in the presence of the compounds synthesized in the Examples with respect to a degree of AMPKα phosphorylation in cells cultured without treatment with the biguanide derivatives. A curve graph showing AMPK activation according to the concentration of the treated compounds was plotted based on the obtained AMPK activation results, and a concentration (activation concentration 150, AC150) value of a compound whose AMPK activation reached 150% was calculated using a GraphPad Prism 5.0 program. Similarly, degrees of AMPK activation when the concentrations of the treated biguanide derivatives of Examples 4 to 61 were 10 μM and 50 μM are listed in the following Table 1, and degrees of AMPK activation when the concentrations of the treated biguanide derivatives of Examples 65 to 98 were 5 μM to 10 μM are listed in the following Table 2. Some of the compounds were not measurable for AMPK activation due to cytotoxicity when the concentrations of the treated compounds were 50 μM.

TABLE 1

| | AMPK activation effect (%) | | |
|---|---|---|---|
| Example | AC150 (μM) | 10 μM | 50 μM |
| Metformin | 188.3 | ND | 130 |
| 4 | 5.0 | 201 | 584 |
| 5 | 2.8 | 235 | 223 |

TABLE 1-continued

| | AMPK activation effect (%) | | |
|---|---|---|---|
| Example | AC150 (μM) | 10 μM | 50 μM |
| 6 | >50 | 124 | 136 |
| 7 | >50 | 94 | 109 |
| 8 | 8.3 | 139 | 515 |
| 9 | 9.0 | 169 | 371 |
| 10 | 1.4 | 408 | — |
| 11 | 1.4 | 637 | — |
| 12 | 13.8 | 97 | 357 |
| 13 | 9.0 | 135 | 462 |
| 14 | 8.4 | 151 | 507 |
| 15 | 1.6 | 554 | — |
| 16 | 1.7 | 398 | — |
| 17 | 4.7 | 208 | — |
| 18 | 0.81 | — | — |
| 19 | 1.5 | 306 | — |
| 20 | 38.3 | 83 | 172 |
| 21 | 11.9 | 156 | — |
| 22 | 24.5 | 116 | 209 |
| 23 | 21.3 | 57 | 279 |
| 24 | 5.3 | 200 | 421 |
| 25 | 2.2 | 376 | — |
| 26 | 0.68 | 443 | 358 |
| 27 | 13.5 | 119 | 316 |
| 28 | 0.15 | 732 | — |
| 29 | 1.3 | 551 | — |
| 30 | 0.53 | 703 | — |
| 31 | 1.8 | 391 | — |
| 32 | 0.62 | 837 | — |
| 33 | 0.79 | 992 | — |
| 34 | 0.29 | 925 | — |
| 35 | 2.4 | 314 | — |
| 36 | 0.87 | 568 | — |
| 37 | 4.2 | 187 | 522 |
| 38 | >50 | 97 | 117 |
| 39 | 67.2 | 96 | 138 |
| 40 | 37.8 | 122 | 163 |
| 41 | 22.4 | 125 | 201 |
| 42 | 14.7 | 157 | 210 |
| 43 | 4.7 | 200 | 466 |
| 44 | 1.7 | 289 | 577 |
| 45 | 4.8 | 202 | 299 |
| 46 | 1.6 | 448 | — |
| 47 | 1.0 | 758 | — |
| 48 | 4.9 | 178 | 691 |
| 49 | 1.9 | 319 | 917 |
| 50 | 1.4 | 317 | 440 |
| 51 | 3.1 | 241 | 409 |
| 52 | 2.7 | 352 | — |
| 53 | 2.3 | 311 | 589 |
| 54 | 0.87 | 545 | 650 |
| 55 | 2.1 | 389 | 608 |
| 56 | 2.1 | 389 | 671 |
| 57 | 2.7 | 279 | 579 |
| 58 | 1.8 | 500 | — |
| 59 | 16.6 | 104 | 283 |
| 60 | 12.4 | 108 | 338 |
| 61 | >50 | 123 | 132 |

TABLE 2

| | AMPK activation effect (%) | | |
|---|---|---|---|
| Example | AC150 (μM) | 5 μM | 10 μM |
| Metformin | 188.3 | | 130 (at 50 μM) |
| 65 | 2.8 | 147 | 274 |
| 66 | 6.2 | 101 | 204 |
| 67 | 1.6 | 258 | 427 |
| 68 | 13.7 | 52 | 136 |
| 69 | 1.2 | 307 | 650 |
| 70 | 0.9 | 365 | 602 |
| 71 | 1.6 | 259 | 430 |

TABLE 2-continued

| | AMPK activation effect (%) | | |
|---|---|---|---|
| Example | AC150 (μM) | 5 μM | 10 μM |
| 72 | 2.0 | 210 | 386 |
| 73 | 2.0 | 215 | 384 |
| 74 | 2.0 | 199 | 410 |
| 75 | 3.9 | 133 | 259 |
| 76 | 1.7 | 242 | 375 |
| 77 | 4.5 | 154 | 212 |
| 78 | 0.5 | 425 | 565 |
| 79 | 1.9 | 177 | 515 |
| 80 | 1.1 | 334 | 590 |
| 81 | 1.9 | 224 | 396 |
| 82 | 0.5 | 401 | 474 |
| 83 | 0.5 | 352 | 398 |
| 84 | 1.1 | 317 | 555 |
| 85 | 0.7 | 345 | 436 |
| 86 | 2.3 | 147 | 330 |
| 87 | 1.9 | 219 | 297 |
| 88 | 0.7 | 327 | 399 |
| 89 | 4.7 | 153 | 198 |
| 90 | 0.8 | 281 | 317 |
| 91 | 5.6 | 108 | 214 |
| 92 | 0.8 | 324 | 417 |
| 93 | 2.0 | 190 | 422 |
| 94 | 1.1 | 328 | 643 |
| 95 | 3.1 | 130 | 326 |
| 96 | 1.8 | 240 | 395 |
| 97 | 4.2 | 143 | 233 |
| 98 | 2.8 | 239 | 244 |

Experimental Example 2: Measurement of Effect of Inhibiting Cancer Cell Proliferation HCT116 cells derived from human colorectal cancer were used, and an effect of inhibiting cancer cell proliferation of the biguanide derivative was confirmed by measuring a concentration value (cell growth inhibition concentration, GIC50) at which cell growth was inhibited by 50% using a 3-(4,5-dimethylthiazol-2-yl)-2,5-diphenyltetrazolium bromide (MTT) reagent.

First, HCT116 cells (purchased from the KCLB) were put on a 96-well plate and cultured in a DMEM medium supplemented with 10% fatal bovine serum (commercially available from Gibco Life Technologies (US)) for 16 hours so that approximately 5,000 cells were counted in each well. Subsequently, to obtain the GIC50 value of each compound, the culture media were treated with 100 μM, 25 μM, 6.25 μM, 1.56 μM or 0.39 μM of the compound, and then cultured for 48 hours. In order to determine whether the cells survived after treatment with the compounds, MTT (commercially available from AMRESCO (US)) was added to the culture media which were then cultured for another 3 hours. Formed formazane crystals were dissolved using dimethyl sulfoxide (DMSO) and the absorbance of the resulting solution was measured at 560 nm. After the 48-hour culture, a ratio of a living cell count on a well plate treated with the compounds synthesized in the Examples to a cell count cultured on a well plate not treated with the compound was indicated as cell viability (%) according to the concentration of each treated compound. The cell viability (%) was used to plot a cell viability curve graph and calculate a concentration (GIC50) value of the compound at which the growth was inhibited by 50%, thereby confirming the inhibition effect of cancer cell proliferation. Also, the cell growth inhibitions (%) when the concentration of the treated biguanide derivative and metformin as the control was 100 μM (Examples 4 to 61) is listed in the following Table 3, and the cell growth inhibitions (%) when the concentration of the treated biguanide derivative and metformin as the control was 25 μM (Examples 65 to 98) are listed in the following Table 4.

TABLE 3

| | Effect of inhibition on cancer cell growth | |
|---|---|---|
| Examples | GI50 (μM) | Cell growth inhibition (%) at 100 μM |
| Metformin | 2172 | 6.5 (at 100 μM) |
| 4 | 19.1 | 99.7 |
| 5 | 18.0 | 99.7 |
| 6 | 12.9 | 99.6 |
| 7 | >100 | 19.8 |
| 8 | 42.8 | 99.1 |
| 9 | 28.8 | 99.5 |
| 10 | 8.3 | 97.9 |
| 11 | 3.0 | 98.0 |
| 12 | 84.8 | 53.8 |
| 13 | 77.1 | 57.8 |
| 14 | 17.5 | 98.8 |
| 15 | 10.1 | 99.2 |
| 16 | 10.8 | 99.3 |
| 17 | 13.9 | 99.7 |
| 18 | 2.6 | 99.5 |
| 19 | 9.1 | 99.6 |
| 20 | 54.8 | 93.1 |
| 21 | 10.4 | 99.4 |
| 22 | 18.6 | 37.1 |
| 23 | 89.9 | 29.5 |
| 24 | 33.9 | 99.0 |
| 25 | 4.9 | 96.6 |
| 26 | 8.2 | 96.7 |
| 27 | 33.5 | 96.6 |
| 28 | 8.4 | 100.5 |
| 29 | 9.5 | 100.4 |
| 30 | 7.5 | 99.7 |
| 31 | 7.8 | 99.5 |
| 32 | 7.9 | 99.4 |
| 33 | 3.7 | 99.4 |
| 34 | 6.6 | 99.4 |
| 35 | 18.4 | 99.1 |
| 36 | 11.2 | 99.0 |
| 37 | 135.0 | 45.3 |
| 38 | 108.5 | 47.8 |
| 39 | 123.7 | 39.8 |
| 40 | >100 | 37.4 |
| 41 | 88.2 | 55.9 |
| 42 | >100 | 14.0 |
| 43 | 114.4 | 44.9 |
| 43 | 114.4 | 44.9 |
| 44 | >100 | 27.8 |
| 45 | 107.2 | 47.2 |
| 46 | 12.0 | 100.1 |
| 47 | 10.8 | 100.0 |
| 48 | 42.5 | 97.6 |
| 49 | 57.0 | 91.8 |
| 50 | 116.8 | 46.0 |
| 51 | 102.5 | 48.7 |
| 52 | 15.4 | 100.1 |
| 53 | 43.7 | 97.9 |
| 54 | 14.6 | 98.1 |
| 55 | 22.8 | 97.9 |
| 56 | 26.9 | 97.7 |
| 57 | 26.9 | 97.8 |
| 58 | 7.9 | 98.4 |
| 59 | 141.4 | 44.5 |
| 60 | 99.8 | 50.1 |
| 61 | >100 | 10.5 |

TABLE 4

| Examples | GI50 (μM) | Cell growth inhibition (%) at 25 μM |
|---|---|---|
| Metformin | 2172 | 6.5 (at 100 μM) |
| 65 | 18.3 | 66.7 |
| 66 | 18.5 | 67.4 |
| 67 | 9.2 | 100.2 |
| 68 | 45.3 | 29.4 |
| 69 | 1.9 | 100.5 |
| 70 | 3.9 | 100.5 |
| 71 | 5.7 | 100.4 |
| 72 | 8.0 | 100.3 |
| 73 | 6.7 | 100.3 |
| 74 | 8.7 | 100.4 |
| 75 | 9.3 | 100.3 |
| 76 | 5.8 | 100.4 |
| 77 | 11.3 | 100.2 |
| 78 | 7.0 | 100.3 |
| 79 | 9.4 | 98.9 |
| 80 | 6.8 | 99.7 |
| 81 | 7.7 | 100.3 |
| 82 | 7.0 | 100.3 |
| 83 | 6.8 | 100.2 |
| 84 | 10.4 | 97.0 |
| 85 | 7.1 | 100.2 |
| 86 | 27.6 | 49.0 |
| 87 | 10.0 | 100.1 |
| 88 | 6.6 | 100.4 |
| 89 | 6.2 | 100.4 |
| 90 | 3.2 | 100.4 |
| 91 | 11.4 | 100.4 |
| 92 | 7.5 | 100.4 |
| 93 | 3.0 | 100.3 |
| 94 | 2.8 | 100.5 |
| 95 | 2.9 | 100.6 |
| 96 | 10.4 | 100.6 |
| 97 | 9.1 | 100.5 |
| 98 | 45.4 | 28.2 |

The invention claimed is:

1. A compound of following Formula 1 or a pharmaceutically acceptable salt thereof:

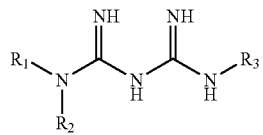

[Formula 1]

wherein $R_1$ and $R_2$ are taken together with nitrogen to which they are attached to form piperidine substituted with not more than one or two methyl groups, wherein the substitution is in at least one of positions 2, 3, 5, and 6; and $R_3$ is $C_{1-6}$ alkyl; or phenyl;

wherein the phenyl is unsubstituted or substituted with at least one non-hydrogen substituent selected from halogen, hydroxy, $C_{1-6}$ alkyl, $C_{1-6}$ alkoxy, $C_{1-6}$ haloalkyl, or $C_{1-6}$ haloalkoxy.

2. The compound of Formula 1 or the pharmaceutically acceptable salt thereof of claim 1, wherein the compound of Formula 1 is N1-(3-methyl)piperidine-N5-(4-fluoro)phenyl biguanide;
N1-(3-methyl)piperidine-N5-(4-bromo)phenyl biguanide;
N1-(3-methyl)piperidine-N5-(4-chloro,3-trifluoromethyl)phenyl biguanide;
N1-(3-methyl)piperidine-N5-(3-fluoro,4-trifluoromethyl)phenyl biguanide;
N1-(3-methyl)piperidine-N5-(4-fluoro,3-trifluoromethyl)phenyl biguanide;
N1-(2-methyl)piperidine-N5-(4-trifluoromethoxy)phenyl biguanide;
N1-(2-methyl)piperidine-N5-(3-trifluoromethoxy)phenyl biguanide;
N1-(2-methyl)piperidine-N5-(4-trifluoromethyl)phenyl biguanide;
N1-(3-methyl)piperidine-N5-(3-fluoro,4-trifluoromethoxy)phenyl biguanide;
N1-(2-methyl)piperidine-N5-(3-fluoro,4-trifluoromethoxy)phenyl biguanide;
N1-(2-methyl)piperidine-N5-(4-chloro)phenyl biguanide;
N1-(2-methyl)piperidine-N5-(4-fluoro,3-trifluoromethyl)phenyl biguanide;
N1-(2-methyl)piperidine-N5-(3-trifluoromethyl)phenyl biguanide;
N1-(2-methyl)piperidine-N5-(4-chloro,3-trifluoromethyl)phenyl biguanide;
N1-(3-methyl)piperidine-N5-(4-trifluoromethyl)phenyl biguanide;
N1-(3-methyl)piperidine-N5-(4-trifluoromethoxy) phenyl biguanide;
N1-(3-methyl)piperidine-N5-(3-trifluoromethoxy)phenyl biguanide;
N1-(3-methyl)piperidine-N5-(4-fluoro,3-trifluoromethyl)phenyl biguanide;
N1-(3-methyl)piperidine-N5-(4-chloro)phenyl biguanide;
N1-(3-methyl)piperidine-N5-(3-trifluoromethyl)phenyl biguanide;
N1-(2,6-dimethyl)piperidine-N5-(4-trifluoromethoxy)phenyl biguanide;
N1-(2,6-dimethyl)piperidine-N5-(3-trifluoromethoxy)phenyl biguanide;
N1-(2,6-dimethyl)piperidine-N5-(4-trifluoromethyl)phenyl biguanide;
N1-(2,6-dimethyl)piperidine-N5-(3-trifluoromethyl)phenyl biguanide;
N1-(2,6-dimethyl)piperidine-N5-(4-fluoro,3-trifluoromethyl)phenyl biguanide;
N1-(2,6-dimethyl)piperidine-N5-(4-chloro,3-trifluoromethyl)phenyl biguanide;
N1-(2,6-dimethyl)piperidine-N5-(3-fluoro,4-trifluoromethoxy)phenyl biguanide;
N1-(2,6-dimethyl)piperidine-N5-(4-chloro)phenyl biguanide;
N1-(2,6-dimethyl)piperidine-N5-(4-bromo)phenyl biguanide; or
N1-(2,6-dimethyl)piperidine-N5-(4-fluoro)phenyl biguanide.

3. A method of treating a cancer, comprising:
administering a therapeutically effective amount of the compound of Formula 1 or the pharmaceutically acceptable salt thereof defined in claim 1 to a subject.

4. The method of claim 3, wherein the method inhibits metastasis of the cancer.

5. The method of claim 3, wherein the cancer is a disease selected from the group consisting of uterine cancer, breast cancer, gastric cancer, brain cancer, rectal cancer, colorectal cancer, lung cancer, skin cancer, blood cancer, pancreatic cancer, prostate cancer, and liver cancer.

* * * * *